US008629103B2

(12) United States Patent
Kleinberg

(10) Patent No.: US 8,629,103 B2
(45) Date of Patent: Jan. 14, 2014

(54) TREATMENT OF NON-PROLIFERATIVE CYSTIC DISEASE OF THE BREAST

(75) Inventor: David L. Kleinberg, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/309,780

(22) Filed: Dec. 2, 2011

(65) Prior Publication Data
US 2012/0141506 A1 Jun. 7, 2012

Related U.S. Application Data

(60) Provisional application No. 61/458,834, filed on Dec. 2, 2010.

(51) Int. Cl.
A61K 38/30 (2006.01)
A61K 38/31 (2006.01)
A61P 5/02 (2006.01)
C07K 14/65 (2006.01)

(52) U.S. Cl.
USPC .............................. 514/7.1; 514/8.6; 514/11.1

(58) Field of Classification Search
None
See application file for complete search history.

(56) References Cited

U.S. PATENT DOCUMENTS

| 6,066,616 | A | 5/2000 | Cavanak et al. |
|---|---|---|---|
| 6,579,967 | B1 | 6/2003 | Rivier et al. |
| 7,432,244 | B2 | 10/2008 | Deshayes et al. |
| 7,473,761 | B2 | 1/2009 | Albert et al. |
| 7,507,769 | B2 | 3/2009 | Nestour |
| 7,648,961 | B2 | 1/2010 | Gougeon et al. |
| 7,838,007 | B2 | 11/2010 | Brin et al. |
| 8,048,927 | B2 | 11/2011 | Le Nestour |
| 2004/0147428 | A1* | 7/2004 | Pluenneke ..................... 514/1 |
| 2005/0014686 | A1 | 1/2005 | Albert et al. |
| 2006/0204540 | A1 | 9/2006 | Kuzma et al. |
| 2009/0203796 | A1 | 8/2009 | Le Nestour |
| 2009/0325863 | A1 | 12/2009 | Kleinberg et al. |

FOREIGN PATENT DOCUMENTS

| GB | 2208200 | * | 3/1989 | ............. A61K 37/43 |
|---|---|---|---|---|
| WO | 0210192 | | 2/2002 | |
| WO | 2005034989 | | 4/2005 | |

OTHER PUBLICATIONS

Weckbecker et al., SOM230: A New Somatostatin Peptidomimetic with Potent Inhibitory Effects on the Growth Hormone/Insulin-Like Growth Factor-I Axis in Rats, Primates, and Dogs, Endocrinology, 143, 4123-4130, 2002.*
Enriori et al., Augmented serum levels of the IGF-I/IGF-binding protein-3 ratio in pre-menopausal patients with type I breast cysts, Eur. J. Endocrinol., 148, 177-184, 2003.*
Arnes et al., "Placental cadherin and the basal epithelial phenotype of BRCA1-related breast cancer", Human Cancer Biology, 2005, vol. 11, pp. 4003-4011.
Chappuis et al., "Cyclin E expression in breast cancer: predicting germline BRCA1 mutations, prognosis and response to treatment", Annals of Oncology, 2005, vol. 16, pp. 735-742.
Evers et al., "Mouse models of BRCA1 and BRCA2 deficiency: past lessons, current understanding and future prospects", Oncogene, 2006, vol. 25, pp. 5885-5897.
Foulkes et al., "Tamoxifen may be an effective adjuvant treatment for BRCA1-related breast cancer irrespective of estrogen receptor status", Journal of the National Cancer Institute, 2002, vol. 94, pp. 1504-1506.
Foulkes et al., "The prognostic implication of the basal-like (Cyclin Ehigh/p27low/p53+/glomeruloid-microvascular-proliferation+) phenotype of BRCA1-related breast cancer", Cancer Research, 2004, vol. 64, pp. 830-835.
Foulkes et al., "Change in the penetrance of founder BRCA1/2 mutations. A retrospective cohort study", J Med Genet, 2002, vol. 39, pp. 407-409.
Hartmann et al., "Benign breast disease and the risk of breast cancer", The New England Journal of Medicine, 2005, vol. 353, No. 3, pp. 229-237.
Kleinberg et al., "Pasireotide, an IGF-I action inhibitor, prevents growth hormone and estradiol-induced mammary hyperplasia", Pituitary, 2011, vol. 14, pp. 44-52.
Laronga et al., "Breast cysts: Diagnosis and management", UpToDate, 2011, retrieved from the Internet <http://www.uptodate.com/store>.
Osin et al., "The pathology of familial breast cancer immunohistochemistry and molecular analysis", Breast Cancer Research, 1999, vol. 1, pp. 36-40.
Robson et al., "A combined analysis of outcome following breast cancer: differences in survival based on BRCA1/BRCA2 mutation status and administration of adjuvant treatment", Breast Cancer Research, 2004, vol. 6, No. 1, pp. R8-R17.

(Continued)

Primary Examiner — Elly-Gerald Stoica
(74) Attorney, Agent, or Firm — Klauber & Jackson LLC

(57) ABSTRACT

The present invention relates generally to the treatment of non-proliferative cystic disease of the breast. More particularly, the present invention relates generally to the treatment of non-proliferative cystic disease of the breast in BRCA1 mutant carriers. Accordingly, the invention relates to the use and application of compounds or agents, including somatostatin analogs, that inhibit insulin-like growth factor I (IGF-I) or insulin-like growth factor I receptor signaling for the treatment of non-proliferative cystic disease of the breast. The invention further relates to the use and application of these compounds or agents for the treatment of non-proliferative cystic disease of the breast in BRCA1 patients. The invention also relates to use of somatostatin analog SOM230 in treatment of non-proliferative cystic disease of the breast and more particularly, to use of somatostatin analog SOM230 in treatment of BRCA1 associated non-proliferative cystic disease.

8 Claims, 15 Drawing Sheets

(56) References Cited

OTHER PUBLICATIONS

Sabel et al., "Overview of benign breast disease", UpToDate, 2011, retrieved from the Internet <http://www.uptodate.com/store>.
Shukla et al., "Absence of the full-length breast cancer-associated gene-1 leads to increased expression of insulin-like growth factor signaling axis members", Cancer Research, 2006, vol. 66, No. 14, pp. 7151-7157.
Wilson et al., "Differential subcellular localization, expression and biological toxicity of BRCA1 and the splice variant BRCA1-delta11b", Oncogene, 1997, vol. 14, pp. 1-16.
Xu et al., "Conditional mutation of BRCA1 in mammary epithelial cells results in blunted ductal morphogenesis and tumour formation", Nature Genetics, 1999, vol. 22, pp. 37-43.
Dupont et al., "Breast cancer risk associated with proliferative breast disease and atypical hyperplasia", Cancer, 1993, vol. 71, No. 4, pp. 1258-1265.
Bajetta et al, "A randomized, multicenter prospective trial assessing long-acting release octreotide pamoate plus tamoxifen as a first line therapy for advanced breast carcinoma", Cancer, 2002, vol. 94, pp. 299-304.
Boccardo et al., "Management of breast cancer: is there a role for somatostatin and its analogs?", Chemotherapy, 2001, vol. 47, pp. 62-77.
Foekens et al., "Prognostic value of receptors for insulin-like growth factor 1, somatostatin, and epidermal growth factor in human breast cancer", Cancer Research, 1989, vol. 49, pp. 7002-7009.
Hofland et al., "Somatostatin analogs: clinical application in relation to human somatostatin receptor subtypes", Biochemical Pharmacology, 1995, vol. 50, No. 3, pp. 287-297.
Hudelist et al., "Intratumoral IGF-I protein expression is selectively upregulated in breast cancer patients with BRCA1/2 mutations", Endocrine-Related Cancer, 2007, vol. 14, pp. 1053-1062.
Ingle et al., "A randomized trial of tamoxifen alone or combined with octreotide in the treatment of women with metastatic breast carcinoma", Cancer, 1999, vol. 85, pp. 1284-1292.
Kleinberg et al., "Growth hormone and insulin-like growth factor-I in the transition from normal mammary development to preneoplastic mammary lesions", Endocrine Reviews, 2009, vol. 30, No. 1, pp. 51-74.
Lamberts et al., "The role of somatostatin and its analogs in the diagnosis and treatment of tumors", Endocrine Reviews, 1991, vol. 12, No. 4, pp. 450-482.
Lamberts et al., "New somatostatin analogs: will they fulfil old promises?", European Journal of Endocrinology, 2002, vol. 146, pp. 701-705.
Maor et al., "Elevated insulin-like growth factor-I receptor (IGF-IR) levels in primary breast tumors associated with BRCA1 mutations", Cancer Letters, 2007, vol. 257, pp. 236-243.
O'Byrne et al., "Phase II study of RC-160 (vapreotide), an octapeptide analogue of somatostatin, in the treatment of metastatic breast cancer", British Journal of Cancer, 1999, vol. 79, No. 9/10, pp. 1413-1418.
Ruan et al., "Progesterone stimulates mammary gland ductal morphogenesis by synergizing with and enhancing insulin-like growth factor-I action", Endocrinology, 2005, vol. 146, No. 3, pp. 1170-1178.
Ruan et al., "SOM230 inhibits insulin-like growth factor-I action in mammary gland development by pituitary independent mechanism: mediated through somatostatin subtype receptor 3?", Molecular Endocrinology, 2006, vol. 20, No. 2, pp. 426-436.
Weckbecker et al., "Antiproliferative effects of the somatostatin analogue octreotide (SMS 201-995) on ZR-75-1 human breast cancer cells in vivo and in vitro", Cancer Research, 1992, vol. 52, pp. 4973-4978.
Ben-Shlomo et al., "Selective regulation of somatostatin receptor subtype signaling: evidence for constitutive receptor activation", Molecular Endocrinology, 2007, vol. 21, No. 10, pp. 2565-2578.
Bontenbal et al., "Feasibility, endocrine and anti-tumour effects of a triple endocrine therapy with tamoxifen, a somatostatin analogue and an antiprolactin in post-menopausal metastatic breast cancer: a randomized study with long-term follow-up", Br J Cancer, 1998, vol. 77, No. 1, pp. 115-122, Abstract only.
Buscail et al, "Inhibition of cell proliferation by the somatostatin analogue RC-160 is mediated by somatostatin receptor subtypes SSTR2 and SSTR5 through different mechanisms", Proc Natl Acad Sci, 1995, vol. 92, pp. 1580-1584.
De Herder et al., "Somatostatin analogue treatment of neuroendocrine tumours", Postgrad Med J, 1996, vol. 72, pp. 403-408.
Di Leo et al., "Biological and clinical evaluation of Lanreotide (BIM 23014), a somatostatin analogue, in the treatment of advanced breast cancer", Breast Cancer Research and Treatment, 1995, vol. 34, pp. 237-244.
Dolan et al., "Treatment of metastatic breast cancer with somatostatin analogues—a meta-analysis", Annals of Surgical Oncology, vol. 8, 2001, No. 3, pp. 227-233.
Helle et al., "Effects of tamoxifen and octreotide LAR on the IGF-system compared with tamoxifen monotherapy", Eur J Cancer, 2005, vol. 41, No. 5, pp. 694-701, Abstract only.
Ingle et al., "Octreotide as first-line treatment for women with metastatic breast cancer", Invest New Drugs, 1996, vol. 14, No. 2, pp. 235-237, Abstract only.
Kidd et al., "Differential cytotoxicity of novel somatostatin and dopamine chimeric compounds on bronchopulmonary and small intestinal neuroendocrine tumor cell lines", Cancer, 2008, vol. 113, No. 4, pp. 690-700.
Koppan et al., "Targeted cytotoxic analogue of somatostatin AN-238 inhibits growth of androgen-independent Dunning R-3327-AT-1 prostate cancer in rats at nontoxic doses", Cancer Research, 1998, 58, pp. 4132-4137.
Lamberts et al., "Drug therapy", The New England Journal of Medicine, 1996, vol. 334, pp. 246-254.
Nagy et al., "Synthesis and biological evaluation of cytotoxic analogs of somatostatin containing doxorubicin or its intensely potent derivative, 2-pyrrolinodoxorubicin", Proc Natl Acad Sci, 1998, vol. 95, pp. 1794-1799.
Pollak, "The potential role of somatostatin analogues in breast cancer treatment", Yale Journal of Biology and Medicine, 1997, vol. 70, pp. 535-539.
Pollak, "Mechanisms of antineoplastic action of somatostatin analogs", Proc Soc Exp Biol Med, 1998, vol. 217, No. 2, pp. 143-152, Abstract only.
Prevost et al., "Growth of human breast cancer cell lines is inhibited by the somatostatin analog BIM23014*", Endocrinology, 1991, vol. 129, No. 1, pp. 323-329.
Pritchard et al., "Randomized trial of tamoxifen versus combined tamoxifen and octreotide LAR therapy in the adjuvant treatment of early-stage breast cancer in postmenopausal women: NCIC CTG MA.14", Journal of Clinical Oncology, 2011, vol. 29, No. 29, pp. 3869-3876.
Raggi et al., "Somatostatin receptors in non-endocrine tumours", Minerva Endocrinol, 2001, vol. 26, No. 3, pp. 149-158, Abstract only.
Saveanu et al., "Somatostatin and dopamine-somatostatin multiple ligands directed towards somatostatin and dopamine receptrs in pituitary adenomas", Neuroendocrinology, 2006, vol. 83, pp. 258-263.
Smith-Jones et al., "DOTA-lancreotide: a novel somatostatin analog for tumor diagnosis and therapy", Endocrinology, 1999, vol. 140, No. 11, pp. 5136-5148.
Sommer et al., "A randomized, double-blind, placebo-controlled, phase 3 trial comparing SMS 201-995 pa LAR plus tamoxifen versus tamoxifen plus placebo in women with locally recurrent or metastatic breast cancer", Zentralbl Gynakol, 2001, vol. 123, No. 10, pp. 557-561, Abstract only.
Szepeshazi et al., "Targeting of cytotoxic somatostatin analog AN-238 to somatostatin receptor subtypes 5 and/or 3 in experimental pancreatic cancers", Clinical Cancer Research, 2001, vol. 7, pp. 2854-2861.
Van Eijck et al., "Somatostatin receptors and breast cancer", The Quarterly Journal of Nuclear Medicine, 1998, vol. 42, No. 1, pp. 18-25.
Weckbecker et al., "Somatostatin analogs for diagnosis and treatment of cancer", Pharmac. Ther., 1993, vol. 60, pp. 245-264.

(56) References Cited

OTHER PUBLICATIONS

Nachtigall et al., "The potential role of the investigational somatostatin analog pasireotide (SOM230) in the treatment of neuroendocrine disorders", Current Opin in Endocrinology & DiAbetes, 2006, vol. 13, pp. 369-376.

Canobbio et al., "Somatuline (BIM 23014) and tamoxifen treatment of postmenopausal breast cancer patients: Clinical activity and effect on insulin-ike growth factor-I (IGF-I) levels", Anticancer Research, 1995, vol. 15, No. 6B, pp. 2687-2690.

Bruns et al., "SOM230: a novel somatostatin peptidomimetic with broad somatotropin release inhibiting factor (SRIF) receptor binding and a unique antisecretory profile", European J of Endocrinology, 2002, vol. 146, No. 99, pp. 707-716.

Pagliacci et al., "Inhibition of human breast cancer cell (MCF-7) growth in vitro by the somatostatin analog SMS 201-995: Effects on cell cycle parameters and apoptotic cell death", Endocrinology, 1991, vol. 129, No. 5, pp. 2555-2562.

"What are the risk factors for breast cancer?", Cancer.org [online], 2011, Retrieved from the Internet:<URL:http://www.cancer.org/cancer/breastcancer/detailedguide/breast-cancer-risk-factors>.

"Polycystic ovary syndrome", U.S. National Library of Medicine, NIH, Medline PLUS [online], Mar. 2010, Retrieved from the Internet: <URL:http://www.nlm.nih.gov/medlineplus/ency/article/000369.htm>.

Kim et al., "Hyperplasia and spontaneous tumor development in the gynecologic system in mice lacking the BRCA-D11 isoform", Molecular and Cell Biology, 2006, vol. 26, No. 18, pp. 6983-6992.

Kim et al., "Hyperplasia and spontaneous tumor development in the gynecologic system in mice lacking the BRCA-delta11 isoform", Molecular and Cellular Biology, 2006, vol. 26, No. 18, pp. 6983-6992.

Del Giudice et al., "Insulin and related factors in premenopausal breast cancer risk", Breast Cancer Research and Treatment, 1998, 47, 111-120.

Hess et al., "Growth factor profiles in breast cyst fluid identify women with increased breast cancer risk", The American Journal of Surgery, 1994, 167, 523-530.

Ng et al., "Altered serum levels of insulin-like growth-factor binding proteins in breast cancer patients", Annals of Surgical Oncology, 1998, 5, 194-201.

\* cited by examiner

TREATMENT OF NON-PROLIFERATIVE CYSTIC DISEASE OF THE BREAST

CROSS REFERENCE TO RELATED APPLICATION

This application claims priority under 35 USC §119(e) from U.S. Provisional Application Ser. No. 61/458,834, filed Dec. 2, 2010, which application is herein specifically incorporated by reference in its entirety.

FIELD OF THE INVENTION

The present invention relates generally to the treatment of non-proliferative cystic disease of the breast, uterus and ovary. The present invention also relates generally to the treatment of BRCA1 associated non-proliferative cystic disease of the breast, uterus, and ovary. Accordingly, the invention relates to the use and application of compounds or agents that inhibit IGF-I receptor engagement and signaling for the treatment of non-proliferative cystic disease of the breast, uterus, and ovary. In a particular aspect, the invention relates to the use and application of compounds or agents, including somatostatin analogs, with effect on, affinity for, or specificity to SSTR3 and/or SSTR5 somatostatin receptors for the treatment of non-proliferative cystic disease of the breast, uterus, and ovary. The invention further relates to the use and application of compounds or agents, including somatostatin analogs, with effect on, affinity for, or specificity to SSTR3 and/or SSTR5 somatostatin receptors for the treatment of non-proliferative cystic disease of the breast and/or prevention or reduction of risk for BRCA1 associated breast cancer when associated with non-proliferative cystic disease of the breast. The invention also relates to use of somatostatin analog SOM230 in treatment of non-proliferative cystic disease of the breast and more particularly, to use of somatostatin analog SOM230 in treatment of BRCA1 associated non-proliferative cystic disease of the breast and/or prevention of BRCA1 associated breast cancer when associated with non-proliferative cystic disease of the breast.

BACKGROUND OF THE INVENTION

A variety of studies have shown that different levels of breast cancer risk can be reliably distinguished on the basis of histologic criteria in women with benign breast disease. See, for example, London et al. *JAMA* 1992, 267:941-4; Palli et al. *Int J Cancer* 1991, 47:703-6; Dupont et al. *N Engl J Med* 1985, 312:146-51; Dupont et al. Cancer 1993, 71:1258-65; Hartmann et al. *N Engl J Med* 2005, 353:229-37. Although the conclusions of these studies vary in some respects, results from the two most recent of these references are reviewed herein. The Hartmann et al. (*N Engl J Med* 2005, 353:229-37) study followed 9087 women for a median of 15 years. The histologic findings were as follows: nonproliferative lesions were noted in 67 percent of women, proliferative lesions without atypia were noted in 30 percent, and atypical hyperplasia was noted in 4 percent. At the closure of the study, 707 study participants had developed breast cancer. The relative risk of breast cancer for the cohort was 1.56 (95 percent confidence interval, 1.45 to 1.68), an increased risk that persisted for at least 25 years after biopsy. The relative risk associated with atypia was 4.24 (95 percent confidence interval, 3.26 to 5.41), as compared with a relative risk of 1.88 (95 percent confidence interval, 1.66 to 2.12) for proliferative changes without atypia and of 1.27 (95 percent confidence interval, 1.15 to 1.41) for non-proliferative lesions. A family history of breast cancer was identified as a risk factor that was independent of histologic findings. These results indicate that non-proliferative lesions are linked to a slightly increased chance of developing breast cancer. The results of Dupont et al. (Cancer 1993, 71:1258-65) suggest that the presence of cysts (a type of non-proliferative disorder) significantly increases breast cancer risk, although this increase is largely restricted to patients with proliferative disease without atypia (PDWA). The Dupont et al. study further indicates that there is no evidence that the presence of cysts affects breast cancer risk in women without proliferative breast disease (PD) or in those with atypical hyperplasia (AH). A fourfold increase in breast cancer risk is, however, observed in women with both cysts and familial history (FH).

Breast cancer is the most common cancer in women and the second leading cause of cancer-related mortality in women. About 10% of breast cancer cases cluster in families. Mutations in the breast cancer susceptibility (BRCA) genes are correlated with a high percentage of these familial cases. Indeed, BRCA1 mutations account for the most common form of genetically inherited breast cancer. Germline mutations of BRCA1 have been detected in approximately 90% of familial breast and ovarian cancers and approximately 50% of familial breast cancer alone (Hill et al. 1997 *Br. J. Surg.* 84, 1334-1339; Casey. 1997. *Curr. Opin. Oncol.* 9, 88-93. Women that inherit germ cell mutations of BRCA1 are at up to 80% risk of developing breast cancer and 50% risk of developing ovarian cancer. BRCA mutation carriers are also typically diagnosed with invasive breast cancer about ten years earlier than patients presenting with sporadic breast cancer. BRCA1 associated cancers, moreover, exhibit distinct histopathology, immunohistochemistry, cytogenetics, and gene expression profiles that differ from those of either non-familial breast cancer cases or BRCA2-related breast cancer.

Even though most BRCA1 mutations lead to estrogen receptor negative breast cancer, treatment with estrogen increases cancer risk in Brca1 disease. Also there is a high degree of hyperplastic lesions in women with mutations in the BRCA1 gene when their breast tissue is examined following prophylactic mastectomies performed to avoid development of breast cancer (Hoogerbrugge N J Clin Oncology 2003, 41-45).

Women with certain hyperplastic lesions of the breast are at high risk for breast cancer. There is clinical evidence that treatment with tamoxifen can prevent the development of cancer by about 50%. Tamoxifen treatment is problematic in that it has many side effects and makes women almost completely estrogen deficient as if they were menopausal. Serious side effects include uterine cancer, pulmonary embolism, strokes. Although well tolerated by some patients, many patients experience one or more unpleasant side effects and some experience life threatening complications as a result of tamoxifen treatment. Indeed, some patients consider the side effects of tamoxifen treatment to be unacceptable.

With respect to BRCA1 mutation carriers, however, even tamoxifen, which is effective in preventing most sporadic breast cancers, is not known to be an effective preventive measure (King M C et al, JAMA 2001 2251-2256). Due to their high risk for developing breast cancer and limited preventive options, many BRCA1 mutation carriers feel compelled to turn to prophylactic bilateral mastectomy as the only proven method for preventing development of breast cancer (Meijers-Heijboer, H N Eng J Med 2001 159-164). Bilateral oophorectomy is also an available option, but is known to be less protective (Rebbeck, T R et al J Natl Cancer Inst 1999, 1475-1479).

Antiestrogens or aromatase inhibitors have also been employed as a means of preventing breast cancer in women with preneoplastic breast lesions such as atypical hyperplasia or ductal carcinoma in situ (DCIS). While effective in women with atypical hyperplasia, these approaches may cause serious side effects and symptoms of menopause which can be intolerable, and also a high incidence of osteoporosis. Ruan et al. have proposed that inhibition of insulin-like growth factor 1 (IGF-I or IGF-1) activity might be able to substitute for estrogen inhibitors because IGF-I is essential for estrogen and progesterone action in the mammary gland (Ruan W et al (2005) Endocrinology 146(3):1170-1178).

Somatostatin and somatostatin-related peptides are a family of peptides that have broad spectrum biological actions and exert suppressive effects on a large variety of cells, usually functioning as inhibitors of hormone secretion. Naturally-occurring peptides have a short half life because they are rapidly inactivated by endogenous peptidases and therefore efforts have been made to develop more stable peptides. The three more extensively tested analogs are SMS 201-995 (octreotide), BIM 23014 (lanreotide) and RC-160 (vapreotide) (Lamberts S W J et al (1991) Endocrin Rev 12:450-482). Somatostatins bind somatostatin receptor(s), with subtypes SSTR-1 to SSTR-5 identified, cloned, and functionally characterized (Patel Y C et al (1995) Life Sci 57:1249-1265; Patel Y C et al (1996) Metabolism 45 (suppl 1):31-38; Reisine T and Bell G I (1995) Endocrin Rev 16:427-442; Buscail L et al (1995) PNAS USA 92:1580-1584; Bell G I and Reisine T (1993) Trends Neurosci 16:34-38). Octreotide (Sandostatin$^R$) and vapreotide have a low affinity for SSTR-1, a high affinity for SSTR-2, and relatively low affinity for SSTR-3 and SSTR-5.

Somatostatin analogs have an established role in the management of patients with pituitary and neuroendocrine tumors but only a potential role in the treatment of solid tumors, including breast cancer. In this tumor type in particular, somatostatin analogs showed limited activity either when used alone or when given in combination with tamoxifen or bromocriptine. Moreover, none of the randomized trials that compared the therapeutic value of the combination of octreotide and tamoxifen versus tamoxifen alone showed any advantage in favor of combined treatment (Pritchard K I et al (2011) Journal of Clinical Oncology, 29:3869-3876). Therefore, although the great majority of trials failed to show major side effects attributable to somatostatin analogs, the use of these compounds was limited to controlled trials (Boccardo, F. and Amoroso D. (2001) Chemotherapy 47:62-77).

The new somatostatin analog called SOM230 prevents mammary development in rats via two mechanisms gland (Ruan, W et al (2006) Mol Endocrinology 20(2):426-436). One of them is an inhibitory effect on growth hormone secretion from the pituitary which can cause reduction of serum IGF-I. The other is a direct inhibition of IGF-I action in the mammary gland as demonstrated by a reduction in IRS-1 phosphorylation in the mammary gland. It has been postulated that this effect of SOM230 is mediated by either somatostatin receptor subtype (SSTR) 3 or 5 and that this causes an increase in IGF binding protein 5 (IGFBP5) which in turn blocks the local action of IGF-I in the mammary gland (Ruan, W et al (2006) Mol Endocrinology 20(2):426-436).

There is clearly a need for improved modalities and compounds for prevention of progression to breast cancer in at-risk individuals. The compound tamoxifen, which is in use for breast cancer prevention, has significant side effects due to its blocking effect of circulating estrogen. While tamoxifen is administered to antagonize estrogen action at the estrogen receptor (ER) in the breast, its systemic effects trigger signs and symptoms consistent with menopause. An alternative treatment that would provide targeted preventive therapy, without causing symptoms or signs of estrogen deficiency.

The citation of references herein shall not be construed as an admission that such is prior art to the present invention.

SUMMARY OF THE INVENTION

In its broadest aspect, the present invention extends to the treatment of non-proliferative cystic disease of the breast and/or the prevention of breast cancer in mammals, particularly in humans, that have non-proliferative cystic disease of the breast using inhibitors of IGF-I receptor signaling, including somatostatin analogs. The present invention also encompasses the treatment of BRCA1 associated non-proliferative cystic disease of the breast, uterus, and ovary in mammals, particularly in humans, using somatostatin analogs. In a particular aspect, somatostatin analogs which preferentially target SSTR3 and/or SSTR5 are effective. Exemplary such analogs are SOM230 and native somatostatin (SS14). Antibodies or small molecule inhibitors of IGF-I engagement of the IGF-I receptor that block IGF-I action in the mammary gland are also envisioned herein. Such small molecule inhibitors would be expected to block IGF-I action at all available IGF-I receptors. PQ401, for example, is a very potent and specific IGF-I receptor inhibitor.

In the present invention, a model of non-proliferative cystic disease of the breast and uterus has been implemented and it has been determined that non-proliferative cystic disease can be inhibited by somatostatin analogs, particularly utilizing exemplary analogs SOM230 and SS14, and by specific IGF-I receptor antibodies and small molecule inhibitors. Each of the tested analogs and inhibitors caused a reduction in the size of non-proliferative cystic lesions of the breast.

In accordance with the present invention, a method for treating or reducing breast or mammary non-proliferative cystic disease in a mammal is presented comprising administering to the mammal a somatostatin analog. Also encompassed herein is a method for providing symptomatic relief to a mammal afflicted with non-proliferative cystic disease of the breast, the method comprising administering to the mammal at least one inhibitor of insulin-like growth factor I (IGF-I) or insulin-like growth factor I receptor signaling.

In a particular embodiment, the mammal is a BRCA1 mutation carrier.

In a particular aspect, the somatostatin analog is selected from SOM230, somatostatin 14 (SS14), SMS 201-995, BIM 23014, BIM23A779, AN-238, RC-121, cyclic somatostatin analog peptide, and somatostatin tumor inhibiting analog. In a more particular aspect, the somatostatin analog preferentially targets the SSTR3 receptor and/or the SSTR5 receptor.

In a particular embodiment, SOM230 or SS14 is administered to the mammal and the administering results in a reduction in the size of non-proliferative cystic lesions in the breast or mammary gland.

In a more particular embodiment, the mammal is a human.

Also encompassed herein, is a method for prevention of breast cancer in a mammal diagnosed with non-proliferative cystic disease of the breast comprising administering to said mammal a compound or agent that modulates IGF-1 in the mammary gland. In a particular embodiment, the mammal has an increased risk of breast cancer. In a more particular embodiment, the mammal has an increased risk for ER positive breast cancer. In an alternate embodiment, the mammal has an increased risk for ER negative breast cancer. In a particular embodiment, the mammal is a BRCA1 mutation carrier. In more particular embodiments, the BRCA1 mutation carrier displays non-proliferative cystic disease of the breast, uterus, and/or ovary.

In an aspect of this method, the compound or agent that modulates IGF-I in the mammary gland is a somatostatin analog, or IGF-I specific receptor blocker. More particularly, the somatostatin analog preferentially targets the SSTR3 receptor and/or the SSTR5 receptor. Even more particularly, the somatostatin analog is selected from SOM230 (which binds to 4 of the 5 SSTs), somatostatin 14 (which binds all of the SSTs), SMS 201-995 (octreotide), BIM 23014 (lanreotide), BIM23A779, AN-238, RC-121, cyclic somatostatin analog peptide, and somatostatin tumor inhibiting analog. Octreotide (Sandostatin$^R$) and vapreotide have a low affinity for SSTR-1, a high affinity for SSTR-2, and relatively low affinity for SSTR-3 and SSTR-5. As described herein, also encompassed is a method for screening to identify compounds or agents that modulate IGF-I, including novel somatostatin analogs. Accordingly, the present methods also encompass use of novel somatostatin analogs identified using the screening methods and assays described herein. In a particular aspect, SOM230 is administered to the mammal and the size of non-proliferative cystic lesions is decreased in the breast or mammary gland.

In a further aspect, use of a somatostatin analog, IGF-I specific receptor antibody, or small molecule inhibitor or a composition thereof for the reduction of or treatment of breast or mammary non-proliferative cystic disease in a mammal is envisioned. In a particular embodiment, the mammal has an increased risk of breast cancer. In a further aspect, use of a composition of a somatostatin analog that preferentially targets the SSTR3 receptor and/or the SSTR5 receptor in the breast, an IGF-I specific receptor antibody, or a small molecule inhibitor for the reduction of breast or mammary non-proliferative cystic disease in a mammal is envisioned. The mammal may have an increased risk of breast cancer and may, more particularly, be a BRCA1 mutation carrier.

In a particular aspect, the use of the inhibitor of IGF-I receptor signaling calls for a composition comprising a somatostatin analog selected from SOM230, somatostatin 14, SMS 201-995 (octreotide), BIM 23014 (lanreotide), BIM23A779, AN-238, RC-121, cyclic somatostatin analog peptide, and somatostatin tumor inhibiting analog. In a further aspect, the use of the composition calls for a composition comprising an IGF-I specific receptor blocker, such as an antibody or small molecule inhibitor of IGF-I action on the IGF-I receptor.

In a further aspect, a method is presented for screening potential compounds or agents effective to reduce breast or mammary non-proliferative cystic disease and/or prevent breast cancer in a mammal with an increased risk of breast cancer comprising: contacting at least one Brca1$^{LoxP}$/Brca1$^{LoxP}$ mouse or a cellular sample isolated therefrom with at least one potential compound or agent and assessing the ability of the at least one compound or agent to reduce insulin-like growth receptor I (IGF-I) action in the Brca1$^{LoxP}$/Brca1$^{LoxP}$ mice or a cellular sample isolated therefrom and/or assessing the ability of the at least one compound or agents to reduce breast or mammary non-proliferative cystic disease in the Brca1$^{LoxP}$/Brca1$^{LoxP}$ mice.

In a particular embodiment, the isolated cellular sample comprises breast cells or mammary gland. In a more particular embodiment, the at least one potential compound or agent reduces at least one morphological and/or histological feature of breast or mammary non-proliferative cystic disease in the Brca1$^{LoxP}$/Brca1$^{LoxP}$ mice. In an even more particular embodiment, the at least one potential compound or agent reduces the number and/or severity of the morphological and/or histological feature of breast or mammary non-proliferative cystic disease in the Brca1$^{LoxP}$/Brca1$^{LoxP}$ mice. It would, thus, also reduce symptoms associated with non-proliferative cystic disease. In a particular embodiment, the compounds or agents are somatostatin analogs.

Also encompassed herein is an assay system for screening of potential compounds or agents effective to reduce signs and symptoms of breast or mammary non-proliferative cystic disease and/or prevent breast cancer in a mammal with an increased risk of breast cancer, wherein said system comprises one or more cellular sample comprising breast cells or mammary gland isolated from at least one Brca1$^{LoxP}$/Brca1$^{LoxP}$ mouse and a plurality of compounds or agents. In a particular embodiment, the isolated cellular sample comprises breast cells or mammary gland. In an aspect of the assay system, the plurality of compounds or agents comprises compounds or agents known to bind to SSTR3 and/or SSTR5 receptors or to block IGF-I receptor activity and/or activation. In an embodiment thereof, the compounds or agents are somatostatin analogs or direct specific inhibitors of IGF-I receptors. In a further embodiment, the compounds or agents may be capable of acting as genomic stabilizers that reduce high levels of genomic instability frequently observed in cancers, particularly BRCA associated cancer.

Other objects and advantages will become apparent to those skilled in the art from a review of the following description which proceeds with reference to the following illustrative drawings.

DETAILED DESCRIPTION

Figure 1:
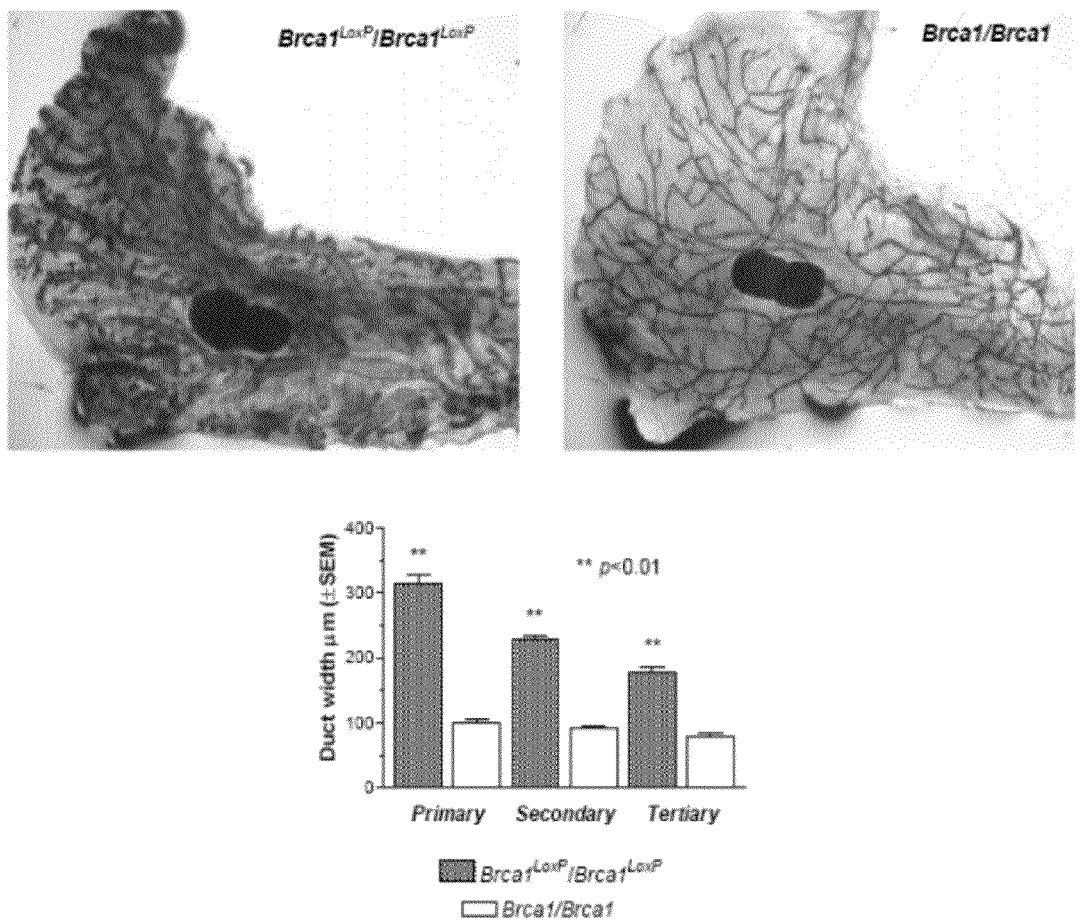
FIG. 1 depicts the mammary gland phenotype in Brca1$^{LoxP}$/Brca1$^{LoxP}$ mice at 4 months of age. Representative whole mounts of mammary glands from a Brca1$^{LoxP}$/Brca1$^{LoxP}$ female and a C57Bl/6 control. The mean width of mammary ducts in five Brca1$^{LoxP}$/Brca1$^{LoxP}$ mice and five C57Bl/6 controls is presented in the graph depicted.

As indicated above, fibrocystic disease of the breast is associated with a slight increased risk for developing breast cancer. See Hartmann et al. (*N Engl J Med* 2005, 353:229-37), the entire contents of which is incorporated herein by reference. The increased risk is more significant when coupled with proliferative disease without atypia (PDWA) or when there is a family history. See Dupont et al. (Cancer 1993, 71:1258-65), the entire content of which is incorporated herein by reference. Indeed, a fourfold increase in breast cancer risk is observed in women with both cysts and familial history (FH). See "Fibrocystic Breast Disease." *MedlinePlus*. 28 Oct. 2004. National Library of Medicine. 8 Nov. 2004 www.nlm.nih.gov/medlineplus/ency/article/000912.htm and Vogel, Victor G. "Fibrocystic Breast Disease." *The Merck Manual of Medical Information*. Ed. Mark H. Beers. 2nd Home ed. Whitehouse Station, N.J.: Merck Research Laboratories, 2003. 1389-1389.

Benign breast disease encompasses a spectrum of disorders that are typically identified as palpable lesions or as abnormalities visualized by various imaging techniques. Although benign breast disease is not a life threatening condition, it often causes physical pain, which can be quite severe, and lasting emotional anxiety. Indeed, in order to establish a diagnosis of benign breast disease, any lesion in question must be evaluated histologically to distinguish it from breast cancer. Such evaluations are frequently invasive, involving repeated needle aspirations, biopsies and ductal lavage, painful, expensive, and stressful for the patient. Once determined, treatment of benign breast disease is generally targeted toward symptomatic relief and patient education.

Benign epithelial breast lesions can be classified histologically into three categories: nonproliferative, proliferative without atypia, and atypical hyperplasia. The degree of cellular proliferation and atypia provide the basis for the above categorization. See, for example, Sabel et al. (UpToDate® Last literature review version 19.3: September 2011; the entire content of which is incorporated herein by reference in its entirety). Nonproliferative epithelial lesions are generally not associated with an increased risk of breast cancer (Schnitt et al. 2003, Am J Surg. Pathol. 27:836; the entire content of which is incorporated herein by reference in its entirety). The most common nonproliferative breast lesions are breast cysts. Other nonproliferative lesions include papillary apocrine change, epithelial-related calcifications and mild hyperplasia of the usual type.

Simple cysts are fluid filled, round or ovoid masses derived from the terminal duct lobular unit. Severe, localized pain may be associated with acute enlargement of cysts in the breast. Papillary apocrine change refers to a proliferation of ductal epithelial cells displaying apocrine features and characterized by eosinophilic cytoplasm. Epithelial related calcifications are benign calcifications that are observed in breast tissue and can be seen in normal ducts and lobules, breast stroma or blood vessel walls. Mild hyperplasia of the usual type is an increase in the number of epithelial cells within a duct that is more than two, but not more than four, cells in depth (Schnitt, S J, Collins, L C. Pathology of benign breast disorders. In: Breast diseases, 4th ed, Harris, J R, et al (Eds), Lippincott, Philadelphia 2010. p69). The epithelial cells do not cross the lumen of the involved space.

More than half of women experience fibrocystic breast changes at some point in their lives. Medical professionals utilize the terms "fibrocystic breasts", "fibrocystic breast changes", or "cystic disease of the breast" to refer to the presence of such changes in a patient. Although the breast changes categorized as "fibrocystic breasts" are normal, they can cause breast pain and swelling, tenderness and lumpiness, especially in the upper, outer quadrant of the breast. Such symptoms tend to be most intense in the second half of the menstrual cycle and/or during pregnancy. Patients typically achieve symptomatic relief by taking over the counter anti-inflammatory and/or pain alleviating medications.

As indicated above, breast cysts can be painful and worrisome, but are generally benign. Indeed, the overall risk of breast cancer is not significantly increased in women with a history of simple breast cysts. See, for example, http://en.wikipedia.org/wiki/Breast_cyst; Laronga et al. (UpToDate® Last literature review version 19.3, September 2011); Dupont et al. (N. Engl. J. Med. 1985, 312:146); and Chun et al. (Am. J. Surg. 2005, 190:583); the content of each of which is incorporated herein by reference in its entirety. That being the case, medical intervention with respect to treating breast cysts is generally not enacted unless the cysts are associated with unacceptable levels of pain and/or discomfort. In most cases, discomfort caused by a breast cyst can be alleviated by draining the fluid from the cyst by needle aspiration. The potential for recurrence of the aspirated cyst or the appearance of new cysts, however, remains. The methods and use of the agents described herein are particularly directed to providing or conferring symptomatic relief to subjects diagnosed with non-proliferative cystic disease of the breast, particularly those that experience unacceptable levels of pain and/or discomfort and/or recurrence of cysts. As used herein and understood in the art, symptomatic relief refers to a reduction in the adverse effects associated with a condition or disease. With respect to a subject diagnosed with non-proliferative cystic disease of the breast, symptomatic relief refers to a reduction in the level of pain, discomfort, and/or lumpiness associated with the disease. The methods and use of the agents described herein thus offer an alternative therapeutic approach to repeated invasive procedures that are presently used to address the disease in some patients.

Tamoxifen and derivatives thereof, such as 4-hydroxy tamoxifen (4-OHT), have been proposed as agents for the treatment of benign breast disease. See, for example, U.S. Pat. Nos. 7,507,769 and 8,048,927. Tamoxifen, however, exhibits significant drawbacks with respect to side-effects, and for many women the side-effects cannot be tolerated. 4-OHT is anticipated to cause fewer side effects, but may still be linked to adverse side effects given its generalized anti-estrogenic properties. Botulinum toxin type A has also been proposed as a potential therapeutic for the treatment of non-malignant mammary gland disorders. See U.S. Pat. No. 7,838,007. In that botulinum toxin type A is rather indiscriminate with respect to specifically targeting the affected tissue, significant side effects may also be linked to its use for the treatment of mammary gland disorders. The present inventors believe that the somatostatin analogs described herein, particularly those which preferentially target SSTR3 and/or SSTR5, may be used to advantage for the treatment of non-proliferative cystic disease of the breast because the analogs are shown herein to be therapeutically effective in animal models of human cystic disease and are anticipated to be exquisitely specific for the target tissue.

Moreover, the present inventor has previously demonstrated that pasireotide, prevents growth hormone and estradiol induced mammary hyperplasia. See Kleinberg et al. (2011, Pituitary 14:44); the content of which is incorporated herein by reference in its entirety. Tamoxifen was also shown to prevent growth hormone and estradiol-induced mammary hyperplasia in the model described therein. With respect to a comparison of the two therapeutic agents, the results of Kleinberg et al. also demonstrate that pasireotide is at least as effective as tamoxifen in preventing growth hormone and estradiol-induced mammary hyperplasia. In view of the favorable therapeutic effect of pasireotide and its relatively mild side effect profile, clinical use of pasireotide offers a more tolerable alternative to treatment with tamoxifen. The benefits of such an alternative clinical approach for any condition, including the treatment of non-proliferative cystic disease of the breast, are underscored by the serious adverse side effects associated with tamoxifen use, some of which are life threatening (e.g., an increased risk of uterine cancer, thromboembolic disease, and stroke) and quality of life issues associated with its use that many patients consider unacceptable.

As indicated above, proteins encoded by the BRCA-1 and BRCA-2 genes have been implicated in predisposition to breast, ovarian and other cancers. These proteins are ubiquitously expressed and functionally linked to a variety of essential cellular processes, including DNA repair and recombination, checkpoint control of cell cycle and transcription. Genetic susceptibility to breast cancer has, moreover, been linked to a variety of mutations of the BRCA1 and BRCA2 genes. BRCA1 mutations, moreover, account for the most common form of genetically inherited breast cancer. Women that inherit germ cell mutations of BRCA1 are at up to 80% risk of developing breast cancer and 50% risk of developing ovarian cancer. Further to the above, inherited mutations in the BRCA1 gene predispose women to early onset breast and ovarian cancers [Alberg et al. 1997. Curr. Opin. Oncol. 9:505-511; Brody et al. 1998. Medicine (Baltimore) 77:208-226]. The BRCA1 gene includes 24 exons that encode proteins of 1,863 and 1,812 amino acids in humans and mice, respectively (Lane et al. 1995. Genes Dev. 9:2712-2722; Miki et al. 1994. Science 266:66-71.23, 27). Full-length human BRCA1 protein (BRCA1-FL) is a nuclear protein of 220 kD. Exon 11, an unusually large exon of 3.4 kb, encodes over 60% of the protein. In addition to BRCA1-FL, BRCA1 also encodes at least two protein products of smaller size due to alternative splicing (ElShamy et al. 2004. Nat. Cell Biol. 6:954-967; Thakur et al. 1997. Mol. Cell. Biol. 17:444-452; Wilson et al. 1997. Oncogene 14:1-16; Xu et al. 1999. Mol. Cell 3:389-395). One of the variants, BRCA1-Δ11 (also termed BRCA1-Δ11b), arises from in-frame splicing between exon 10 and exon 12, and retains the highly conserved amino-terminal RING finger and carboxyl-terminal BRCT domains of full-length BRCA1. The other variant is BRCA1-IRIS, which is a 1,399-residue polypeptide encoded by an uninterrupted open reading frame that extends from codon 1 of the known BRCA1 open reading frame to a termination point 34 triplets into intron 11 (ElShamy et al. 2004. Nat. Cell Biol. 6:954-967). BRCA1 has been shown to be involved in controlling genetic stability, DNA damage repair, centrosome duplication, apoptosis, and cell cycle control (reviewed in references Deng. 2002. Oncogene 21:6222-6227; Deng et al. 2003. Hum. Mol. Genet. 12:R113-R123; Venkitaraman. 2002. Cell 108:171-182; Zheng et al. 2000. Oncogene 19:6159-6175).

From a clinical standpoint, BRCA1-related tumors demonstrate distinct features with regard to histopathology (Breast Cancer Linkage Consortium. Lancet 1997; 349: 1505-1510), immunohistochemistry (IHC) (Lakhani et al. J Clin Oncol 2002; 20: 2310-2318), cytogenetics (Tirkkonen et al. Cancer Res 1997; 57:1222-1227) and gene expression profiles (Hedenfalk et al. N Engl J Med 2001; 344: 539-548; van't Veer et al. Nature 2002; 415:530-536) when compared with either non-familial breast cancer cases or BRCA2-related breast cancer. See also Osin et al. www.breast-cancer-research.com/vol1no1/27oct99/review/3; Foulkes et al. Cancer Res 2004; 64:830-835). In particular, BRCA1-related breast cancers tend to be high-grade (Lakhani et al. 2002; supra), lymph node-negative (Foulkes et al. Cancer (Phila.), 98: 1569-1577, 2003) tumors that do not express estrogen receptors (ERs), progesterone receptors (PR), HER2 (Chappuis et al. Semin. Surg. Oncol., 18: 287-295, 2000), or the tumor suppressor gene $p27^{Kip1}$ (Chappuis et al. J. Clin. Oncol., 18:4045-4052, 2000), but do express p53 (Greenblatt et al. Cancer Res., 61: 4092-4097, 2001), cyclin E (Chappuis et al. Annals of Oncol., 16:735-742, 2005) and cytokeratin (CK) 5/6 (Sørlie et al. Proc. Natl. Acad. Sci. USA, 100: 8418-8423, 2003; Foulkes et al. J. Natl. Cancer Inst. (Bethesda), 95: 1482-1485, 2003). The disclosures of all of the above cited references are incorporated herein in their entireties.

Foulkes et al. (Cancer Res 2004; 64:830-835) also analyzed data using a parsimonious multivariable proportional hazards model and confirmed that germ-line BRCA1 mutations result in breast cancers that are predisposed to be basal in character, as defined by CK5/6 IHC; and demonstrated that the basal phenotype is also characterized by large tumors that express low levels of ER, PR, HER2, and p27Kip1 and high levels of cyclin E, and that feature both nuclear p53 and intratumoral vascular nests (GMP); all of these factors are associated with a poor outcome in univariate analysis; those tumor markers most closely linked to the basal phenotype (p53, p27Kip1, cyclin E, and GMP) are independent predictors of outcome; and the relationship between tumor size and nodal status is significantly different when comparing tumors that do, and do not, express CK5/6. The authors conclude that the basal phenotype of breast cancer deserves recognition as a separate biological entity. The combined association and survival data presented by Foulkes et al. (Cancer Res 2004; supra) suggest that much of the inferior survival after breast cancer that is experienced by BRCA1 carriers (particularly among women with lymph node-negative disease) is attributable to the basal epithelial phenotype of these cancers.

In light of the above, there is more than sufficient evidence to establish BRCA1 associated disease as a distinct subtype of breast cancer having distinct clinicopathological features. The course of BRCA1 related breast cancer is best seen in animal models. In humans, the course is varied. Onset of breast cancer, however, manifests at a younger age in BRCA carriers, than in non-BRCA patients. Cancer onset occurs usually when women are in their 40s. The participation of premalignant lesions is difficult to map out in women as they have many different mutations and therefore, different, presentations. Since prophylactic mastectomy has become more common, information is now available indicating that at the time of mastectomy the prevalence of premalignant disease is high. Hoogerbrugge found that 57% of women had high risk histopathologic lesions; 37% had atypical lobular hyperplasia, 39% atypical ductal hyperplasia, 25% lobular carcinoma in situ, and 15% ductal carcinoma in situ. The women in the study were 27 to 52 years old. Some had undergone a previous mastectomy for carcinoma and were having their second breast removed. The cancer that usually develops in such women is triple negative [negative for estrogen receptors, progesterone receptors, and human epidermal growth factor receptor 2 (HER2)]. The same pattern is observed in the animal models.

Figure 14:
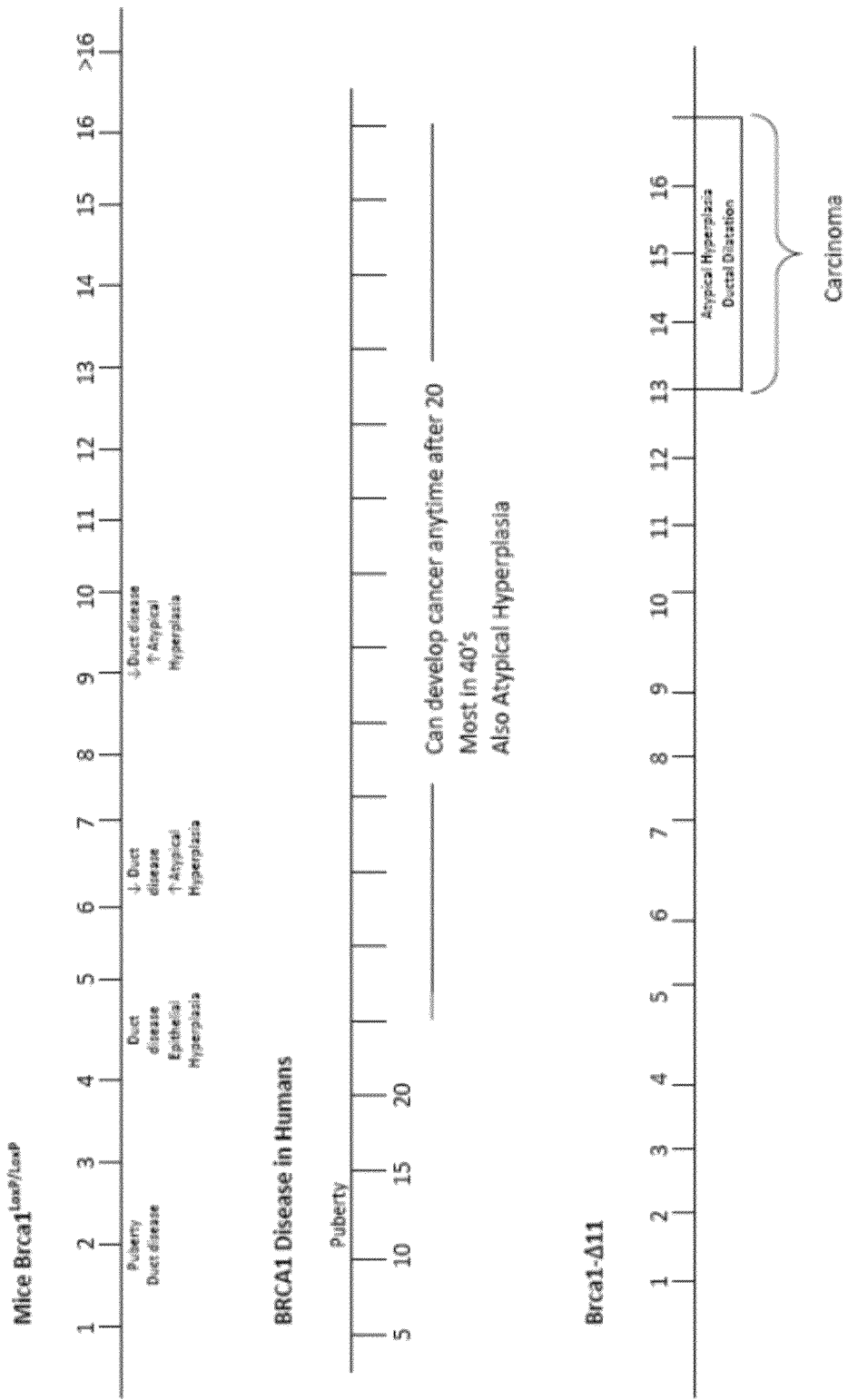
FIG. 14 shows a comparative time line for both Brca1$^{loxP/loxP}$ and Brca1-Δ11 mice and a sample human lifespan and typical age of disease manifestation. Mice have a lifespan of approximately 2 years, and women live for approximately 80 years.

To further investigate BRCA1 associated disease, scientific research has focused on studying animal models of Brca1 deficiency. Unfortunately, mice homozygous for point mutations of Brca1 die in utero. For that reason investigators have turned to conditional deletions of the main exon of Brca1 (exon 11) by a Cre-LoxP approach (Xu et al. 1999, Nature Genetics 22:37-43). This makes the animals deficient in the full length BRCA1 protein. This serves as an acceptable model in some respects, but the model is limited in that mammary tumor formation occurs only after long latency. Mammary carcinomas were eventually observed in 10-13 month old mice. Moreover, breeding is difficult and this makes difficult the testing of large numbers of animals. Accordingly, the animal model system disclosed by Xu et al. is limited with respect to understanding BRCA1 associated disease in human patients, at least in part because the system fails to recapitulate the typical early onset pattern of disease manifestation observed in human BRCA1 carriers. By way of comparison, FIG. 14 illustrates a comparative timeline of human lifespan and typical onset of disease manifestation in BRCA1 carriers as compared to that determined for the BRCA1 conditional mutant mice described by Xu et al. FIG. 14 illustrates that the onset of disease in BRCA1 conditional mutant mice described by Xu et al., which occurs at an advanced age.

Kim et al. (Mol Cell Biol 2006, 26:6983-6992) have developed a different BRCA1 mutated animal model that is deficient in the BRCA1 protein obtained by alternative splicing of Exon 11 (BRCA1 Δ11). In addition to developing late onset breast carcinoma, these animals have abnormalities in mammary ducts and have many areas of hyperplasia. They also have uterine and ovarian abnormalities. Like Xu et al., Kim et al. report that female mice exhibit mammary gland abnormalities and uterine hyperplasia with spontaneous tumor formation, but only after a year of age. The animal model system disclosed by Kim et al. is, therefore, also limited with respect to understanding BRCA1 associated disease in human patients, at least in part because the system fails to recapitulate the typical early onset pattern of disease manifestation observed in human BRCA1 carriers. See also FIG. 14.

Figure 15:
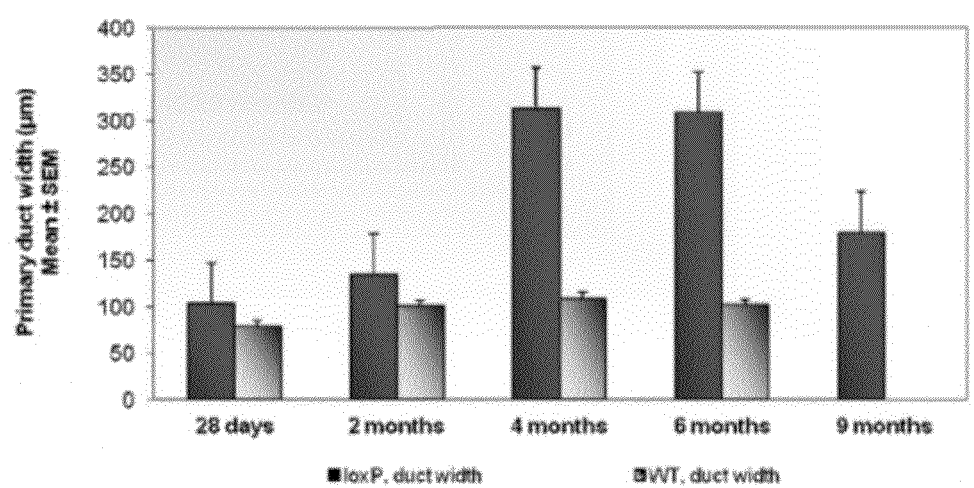
FIG. 15 depicts a histogram showing a comparison of the primary duct width of Brca1$^{LoxP}$/Brca1$^{LoxP}$ mice and normal wildtype (WT) mice at the indicated ages.

In the process of developing animals with a conditional deletion of exon 11, the present inventor made the novel discovery that mice with loxP sites flanking exon 11 (LoxP animals), before being crossed with MMTV-Cre carriers, exhibit an extreme phenotype of the mammary glands and the uteri. The mammary glands of LoxP mice have dilated ducts and areas of dysplasia and hyperplasia. See, for example, FIGS. 1-2. By the age of 4 months, HAN-like lesions (abnormal preneoplastic lesions) were observed in these animals. Hyperplastic dilated uteri are also noted in LoxP mice. FIG. 1 shows a whole mount mammary gland from a 4 month old affected animal, referred to therein as a "LoxP" animal. The term $Brca1^{LoxP}/Brca1^{LoxP}$ mice is used interchangeably with "LoxP" mice and each of these terms refers to the same strain of mice. It is shown together with a mammary gland from an age matched C57Bl/6 mouse. Below the whole mounts, we present mean duct width in the LoxP vs. control animals. See also FIG. 15 which shows a comparison of duct width for LoxP and control animals at the indicated ages.

Figure 2:
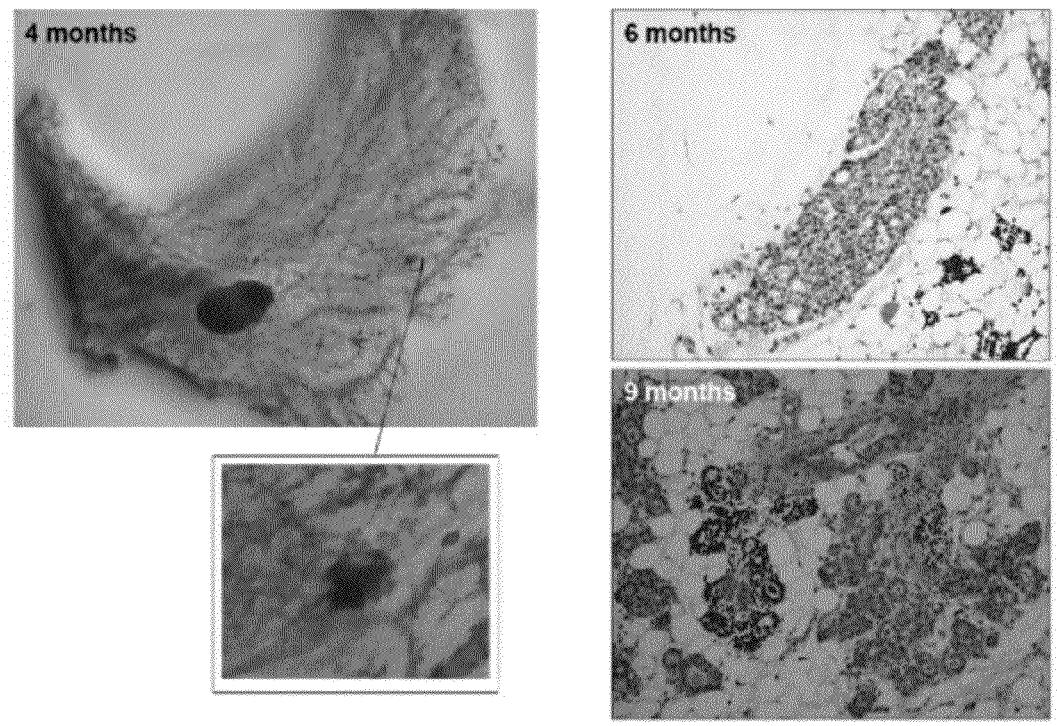
FIG. 2 shows hyperplastic alveolar nodules (HAN) in Brca1$^{LoxP}$/Brca1$^{LoxP}$ mice. Representative whole mount (left) and hematoxylin-eosin stained sections of the HAN-like lesions that can be observed in mammary gland from Brca1$^{LoxP}$/Brca1$^{LoxP}$ females starting from the age of 4 months.

By 28 days of age, LoxP animals begin to exhibit developmental abnormalities and these continue until at least 9 months. More particularly, by two months of age, the mammary gland phenotype in Brca1$^{LoxP}$/Brca1$^{LoxP}$ and C57Bl/6 control mice are phenotypically distinct. See FIG. 12. Brca1$^{LoxP}$/Brca1$^{LoxP}$ mice have terminal end buds, a sign of ongoing mammary development, whereas control mice lack such features. No ductal or lobular hyperplasia, however, is observed in two month old Brca1$^{LoxP}$/Brca1$^{LoxP}$ mice. Another notable phenotypic distinction observed in two month old Brca1$^{LoxP}$/Brca1$^{LoxP}$ mice is the presence of enlarged ducts, which are not apparent in age matched C57Bl/6 control mice. The peak ductal width abnormality occurs at 4 months of age in Brca1$^{LoxP}$/Brca1$^{LoxP}$ mice, while the prevalence of hyperplastic lesions increases with age. FIG. 2 shows examples of a preneoplastic HANs at 4, 6 and 9 months of age.

Relatively speaking, two month old mice are in late puberty and four month old mice are adults. See FIG. 14. Accordingly, the early onset of abnormalities that present in Brca1$^{LoxP}$/Brca1$^{LoxP}$ mice are interesting in several respects. The early onset of the phenotype of non-proliferative cystic lesions in Brca1$^{LoxP}$/Brca1$^{LoxP}$ mice, as evidenced by ductal dilation, facilitates examination of phenotypic risk factors that appear earlier in life, in advance of benign hyperplastic disease onset. The present inventor believes that the appearance of non-proliferative cystic lesions in Brca1$^{LoxP}$/Brca1$^{LoxP}$ mice recapitulates aspects of early disease onset believed to occur in BRCA1 associated disease in humans. No one has performed a study of the age at which such lesions occur in BRCA1 mutated patients, but almost 40% of BRCA1 patients have such lesions by the time they have elected to have prophylactic mastectomies, and breast cancer in BRCA1 patients can appear in the early 20s.

Moreover, although the phenotype of two month old Brca1$^{LoxP}$/Brca1$^{LoxP}$ mice is profoundly abnormal, it is less cystic than that observed in four month old Brca1$^{LoxP}$/Brca1$^{LoxP}$ mice and does not have areas of atypical hyperplasia characteristic of the four month old animals. These results suggest that there is a temporal cascade of hyperactive mammary development, including ductal dilation (cystic disease), that develops by late puberty in Brca1$^{LoxP}$/Brca1$^{LoxP}$ mice (at two months) and evolves into a phenotype of greater duct dilation and the beginning of atypical hyperplasia, as observed in adult Brca1$^{LoxP}$/Brca1$^{LoxP}$ mice (at four months). As Brca1$^{LoxP}$/Brca1$^{LoxP}$ mice age as adults, the ducts fail to enlarge further and may indeed decrease in size, while atypical hyperplasia reaches a maximal level. These findings support a progression from non-proliferative cystic disease of the breast to cystic disease in combination with atypical hyperplasia, which in turn, leads to malignant breast cancer. This progressive cascade from non-proliferative cystic disease of the breast, to cystic disease in combination with atypical hyperplasia, to malignant breast cancer clearly applies to human BRCA1 carriers and likely applies to patients with highly symptomatic fibrocystic disease which consists of breast lumps and breast pain and tenderness.

Accordingly, the early phenotypic changes observed with the Brca1$^{LoxP}$/Brca1$^{LoxP}$ (LoxP) animal model system described herein demonstrates that this is a valid model system for further investigations directed to understanding BRCA1 associated disease in human patients, at least in part because the system recapitulates the typical early onset pattern of disease manifestation observed in human BRCA1 carriers. It also applies to human patients with highly symptomatic fibrocystic disease who may be at higher risk of developing breast cancer. The LoxP animal model system also facilitates evaluating preventive and treatment paradigms without having to wait for unduly long periods of time to observe potential effects on disease manifestation and/or progression and without having to maintain large numbers of animals.

To characterize the LoxP animal model system further, the present inventor assessed Brca1 Δ11 expression to determine if the levels of Brca1 Δ11 were decreased when compared to wildtype levels. First, the levels of Brca1 Δ11 mRNA in LoxP animals were determined and compared to controls. A significant difference in levels of Brca1 Δ11 mRNA, as assayed by either qualitative or quantitative RT-PCR, was not observed in the LoxP animals when compared to controls. See FIG. 3. In contrast, the expression of the Δ11 protein was decreased in comparison to wild type animals. FIG. 4 depicts a representative Western blot showing a band of protein of approximately 80 kDa, which is the molecular weight of the BRCA1 Δ11 protein (Bachelier et al. 2000, Int J Cancer 88:519-524). In contrast the full length protein is expressed similarly in controls and LoxP animals. These results suggest that the phenotypic changes observed in the LoxP animal model system are at least in part due to impaired expression of Brca1 Δ11.

Although not wishing to be bound by theory, the phenotypic changes observed in the LoxP animal model system also appear to be due at least in part to the presence of the LoxP sites in the full length (FL) BRCA1 transcript. This assertion is made based on several lines of reasoning, including the fact that 1) when crossed with MMTV cre, which results in removal of the LoxP sites and intervening exon 11, the phenotype of the LoxP animals is reduced; 2) when crossed to wildtype animals, the phenotype of the LoxP animals is reduced; and 3) the phenotype described by Kim et al., wherein only FL BRCA1 is made in an animal model system, is far less severe than that observed in the LoxP animal model system described herein, wherein only the FL BRCA1 protein is made, but it includes LoxP sites.

As a consequence of the above, it is reasonable to suggest that the phenotypic presentation of the LoxP animal genotype reflects a "double hit" to the BRCA1 proteins, whereby not only is the expression of the Brca1 Δ11 truncated form of BRCA1 impaired, but the activity of FL BRCA1 is altered and/or impaired by the presence of at least one of the LoxP sites. Again, although not wishing to be bound by theory, the impaired activity of FL BRCA1 could be due to generally altered activity (e.g., tumor suppressor activity) of the FL BRCA1 FL transcript due to the presence of at least one of the LoxP sites; impaired nuclear localization of the FL BRCA1 due to the presence of at least one of the LoxP sites, and/or altered interaction with other cellular components that interact directly or indirectly with the FL BRCA 1 wild type protein due to the presence of at least one of the LoxP sites.

Further to the above, the LoxP animal model resembles, in some respects, systems wherein expression of full length BRCA1 is impaired (Skukla et al. 2006, Cancer Res 66:7151-7157). Like those of mice homozygous for targeted deletion of full length BRCA1, the mammary glands of LoxP animals have increased IGF-I activity as measured by phosphorylation of IGF-IR and its downstream mediators ERK and AKT. See, for example, FIG. 5.

The present inventor and colleagues have previously shown that growth hormone induced IGF-I activity is essential for mammary development and also estrogen and progesterone action. To determine whether inhibition of IGF-I action would prevent, reverse or delay the abnormalities associated with BRCA deficiency observed in LoxP animals, affected animals were treated with three different compounds that inhibit IGF-I action. Pasireotide, for example, has been shown by the present inventor and colleagues to inhibit IGF-I action in the mammary gland (Ruan et al. 2006, Mol Endocrinol 20:426-436. Pasireotide is a somatostatin analog that binds to 4 of the 5 somatostatin receptors. Somatostatin 14 (SS14), which binds to all of the somatostatin receptors, and an IGF-I receptor blocker (PQ401) were also utilized. The latter two are both available commercially, whereas the pasireotide is a product of Novartis. As described in the Examples and shown in the Figures presented herein, each one of the drugs is effective in reversing or preventing the LoxP mammary phenotype. See, for example, FIGS. 7-11 and 13. In sum, each of these drugs reduced duct width, glandular hyperplasia and hyperplastic alveolar nodules and tended to normalize the architecture of the mammary glands. Both pasireotide and PQ401 also significantly reduced cell proliferation as assessed by Ki67 immunohistochemistry.

Figure 6:
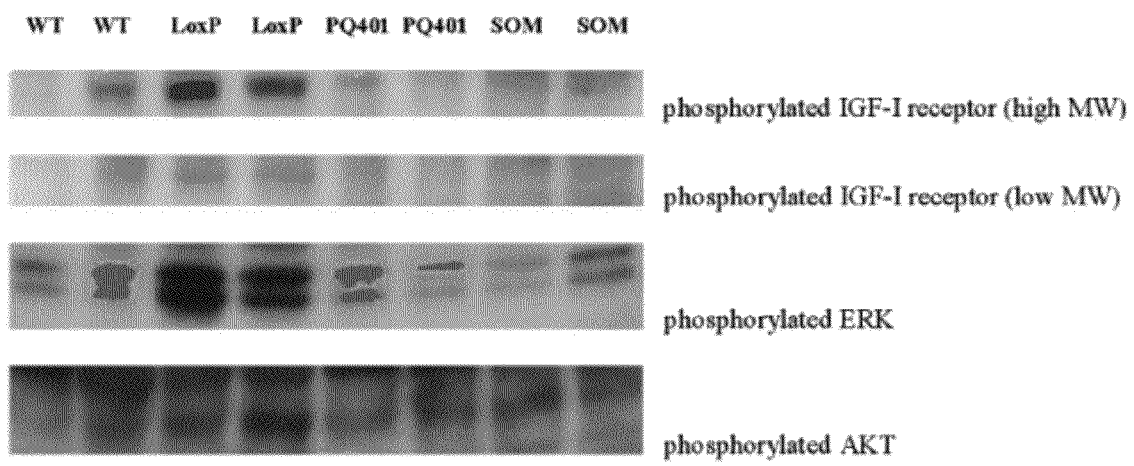
FIG. 6 shows effects of IGF-I inhibition on the phosphorylation of IGF-I receptor, ERK, and AKT in 4 month old Brca1$^{LoxP}$/Brca1$^{LoxP}$. Western blots showing that the increased phosphorylation of IGF-I receptor and its downstream mediators ERK and AKT in Brca1$^{LoxP}$/Brca1$^{LoxP}$ females is reduced by treatment with 100 mg/kg PQ401 thrice a week and 10 µg/kg/h pasireotide. The two WT samples are from age-matched, untreated C57Bl/6 control mice. PQ401 was administered by intraperitoneal injections, pasireotide by Alzet pump Model 2001. For both drugs, the course of treatment was 7 days.
Figure 8:
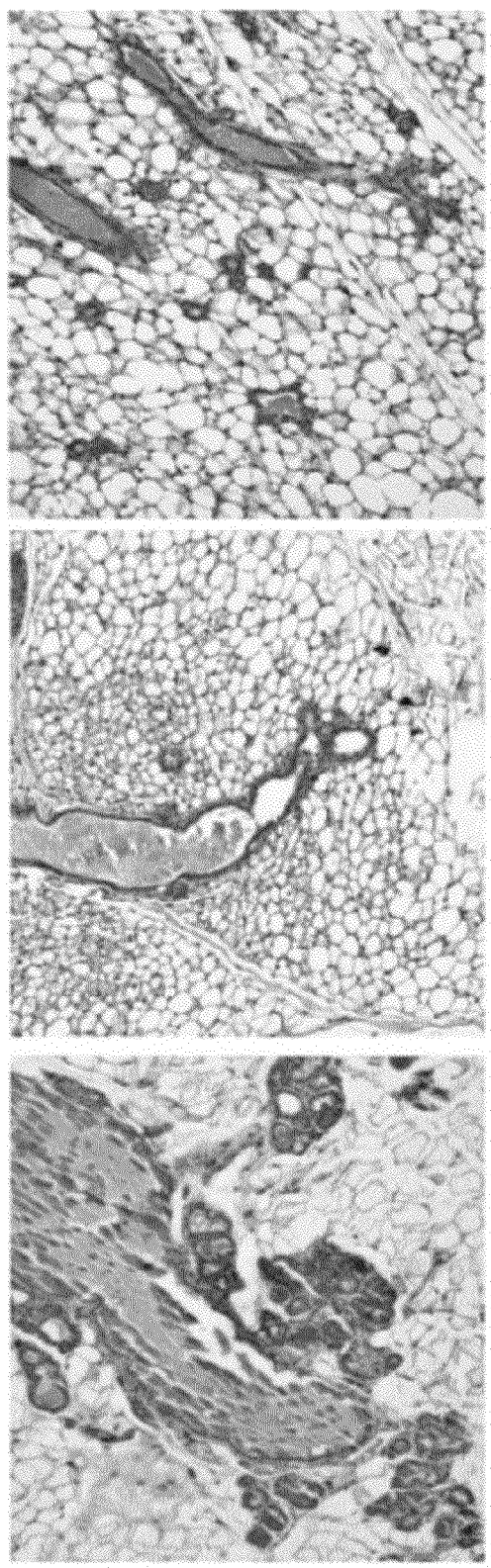
FIG. 8 depicts effects of pasireotide on the mammary gland phenotype of Brca1$^{LoxP}$/Brca1$^{LoxP}$ mice. Representative hematoxylin-eosin sections of mammary glands from 4 month old Brca1$^{LoxP}$/Brca1$^{LoxP}$ females treated with water (left) or pasireotide (center and right) for 7 days. Both water and pasireotide were administered by Alzet pump Model 2001. The dosage of pasireotide was 10 µg/kg/h.
Figure 9:
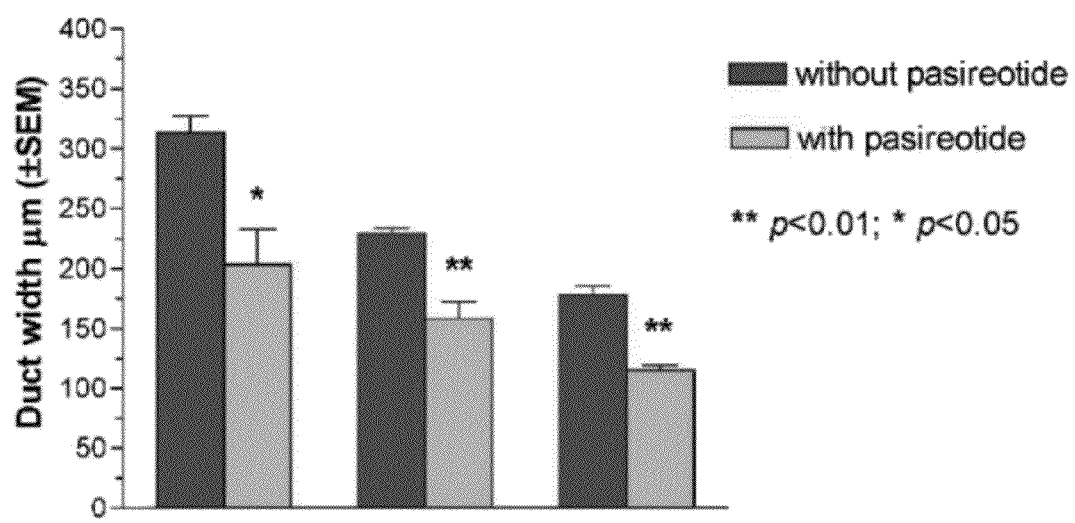
FIG. 9 depicts effects of pasireotide on duct width of mammary glands of Brca1$^{LoxP}$/Brca1$^{LoxP}$ mice. The graph shows that 10 µg/kg/h pasireotide for 7 days is effective in decreasing the width of mammary gland ducts in 4 month old Brca1$^{LoxP}$/Brca1$^{LoxP}$ females, as compared with vehicle (water). Both water and pasireotide were administered by Alzet pump Model 2001. Six animals were treated with pasireotide and five animals were treated with water (control).
Figure 10:
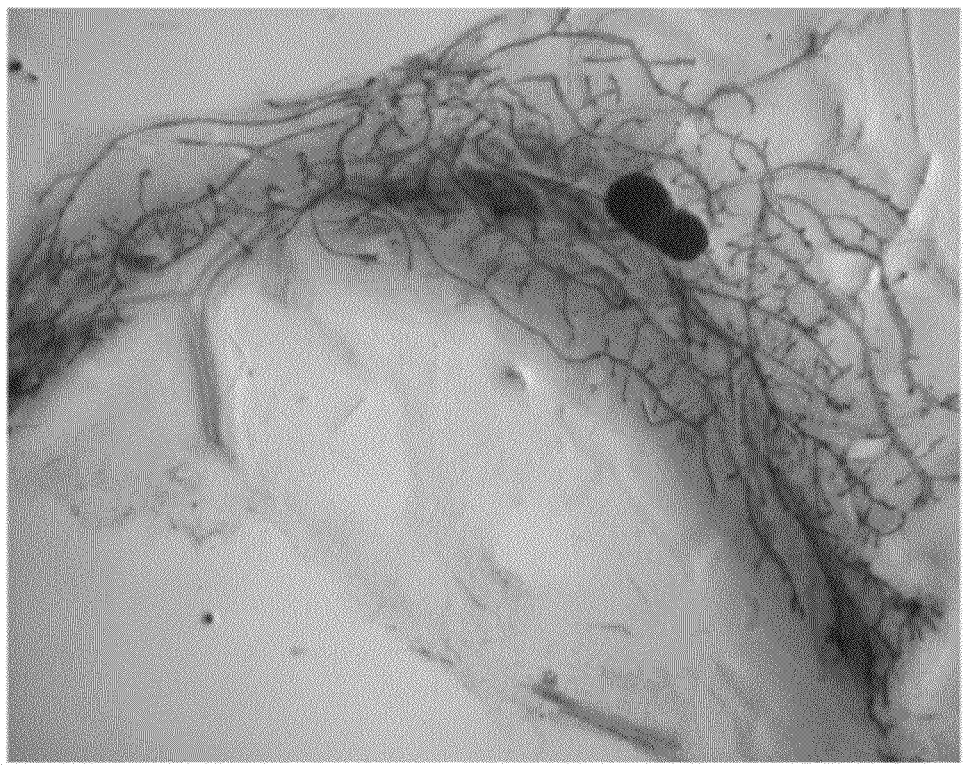
FIG. 10 depicts effects of PQ401 on the mammary gland phenotype of Brca1$^{LoxP}$/Brca1$^{LoxP}$ mice. Representative whole mounts from mammary glands of 4 month old Brca1$^{LoxP}$/Brca1$^{LoxP}$ females treated with PQ401 (upper microphotograph) or vehicle (8% ethanol/Tween 80 in PBS, lower microphotograph) for 7 days. Both PQ401 and vehicle were administered by intraperitoneal injections.
Figure 10:
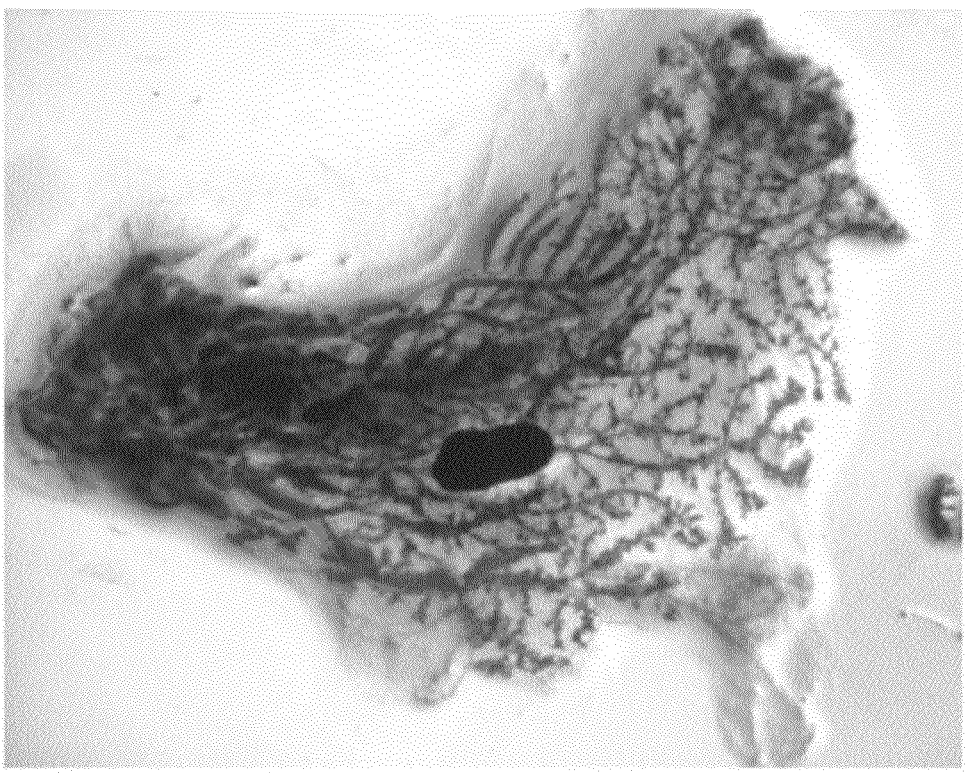
Figure 11:
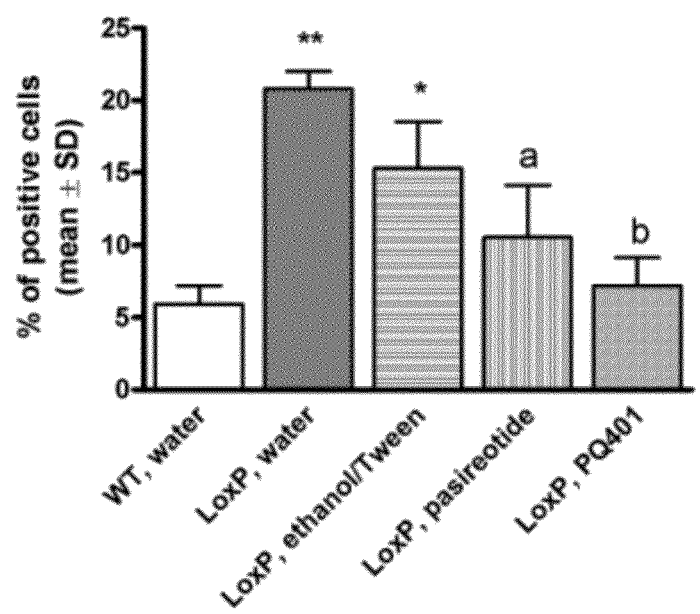
FIG. 11 shows the percentage of Ki67-positive epithelial cells in the mammary glands of 4 month old Brca1$^{LoxP}$/Brca1$^{LoxP}$ mice after 7 days of treatment with pasireotide (LoxP, pasireotide), PQ401 (LoxP, PQ401), or vehicle (LoxP, water and LoxP, ethanol/Tween). The frequency of Ki67-positive mammary epithelial cells in C57Bl/6 controls treated with water (WT, water) is also presented. *, $p<0.05$ as compared with WT, water; **, $p<0.01$ as compared with WT, water; a, $p<0.05$ as compared with LoxP, water; b, $p<0.01$ as compared with LoxP, water.

Pasireotide and PQ401 also reduced the phosphorylation of IGF-IR and of ERK and AKT (FIG. 6). These drugs were used for 7 days vs. vehicle in 4 month old LoxP and control animals. The effects of pasireotide in 4 month old Lox P animals vs controls are also shown on whole mounts (FIG. 7), glandular histology (FIG. 8), and duct width (FIG. 9). Four month old animals were also treated with PQ401 for 7 days. This IGF-I receptor blocker achieved a similar effect (FIG. 10). Both pasireotide and PQ401 inhibited cell proliferation (FIG. 11). Nine month old animals were treated with SS14 for week. Prevention or reversal of the phenotype and impressive reduction in the number of HANs was observed following treatment with SS14.

As described herein, the LoxP animal model system is useful for assaying the efficacy of IGF-I inhibitors in the prevention and/or inhibition of cystic disease of the breast and hyperplastic disorders of the breast. As further described herein, proliferative disorders of the breast include: fibroadenoma, intraductal papilloma, atypical ductal hyperplasia, and atypical lobular hyperplasia. In a particular aspect, the proliferative disorder involves precancerous and/or cancerous lesions in BRCA1 mutation carriers. In a more particular aspect, the LoxP animal model system is useful for assaying the efficacy of IGF-I inhibitors in the prevention of cancer in BRCA1 mutant carriers. The LoxP animal model system is, furthermore, useful for assaying the efficacy of IGF-I inhibitors in the prevention and/or inhibition of other patients having a genetic predisposition to cancer.

The LoxP animal model system is also useful for assaying the efficacy of agents or compounds in the prevention and/or inhibition of cystic disease of the breast and in symptomatic relief thereof. As described herein, assaying may be performed to evaluate the efficacy of agents or compound in the prevention and/or inhibition of proliferative disorders of the breast, including: fibroadenoma, intraductal papilloma, atypical ductal hyperplasia, and atypical lobular hyperplasia. In a particular aspect, the proliferative disorder involves precancerous in BRCA1 mutation carriers. In a more particular aspect, the LoxP animal model system is useful for assaying the efficacy of agents or compounds in the prevention of cancer in BRCA1 mutant carriers. The LoxP animal model system is, furthermore, useful for assaying the efficacy of agents or compounds in the prevention and/or inhibition of cancer in other patients having a genetic predisposition to cancer.

Therefore, if appearing herein, the following terms shall have the definitions set out below.

As used herein, the term "cystic disease", or "fibrocystic disease" of the breast refers to a benign disease common in women in their thirties, forties and fifties, marked by small fluid containing cysts that form in one or both breasts and associated with stromal fibrosis and varying degrees of intraductal epithelial hyperplasia and sclerosing adenosis.

As used herein, the term "non-proliferative cystic disease", or "non-proliferative fibrocystic disease" of the breast refers to a benign condition or disease common in women in their thirties, forties and fifties, marked by small fluid containing cysts that form in one or both breasts and associated with stromal fibrosis, and lacking detectable regions of atypical hyperplasia.

As used herein, "highly symptomatic fibrocystic disease" is characterized by the presence of breast lumps and breast pain and tenderness. In the absence of detectable regions of atypical hyperplasia, the term "highly symptomatic non-proliferative fibrocystic disease" may be used to define a patient population for treatment as described herein. Use of agents and/or compositions as described herein to alleviate symptoms associated with "highly symptomatic non-proliferative fibrocystic disease" is also encompassed herein.

As used herein, mild hyperplasia of the usual type is an increase in the number of epithelial cells within a duct that is more than two, but not more than four, cells in depth.

As used herein, the term "atypical hyperplasia" describes an accumulation or increased number of abnormal cells.

As used herein, the term "adenosis" refers to generalized glandular disease of the breast. It typically involves an enlargement of breast lobules, which contain more glands than usual. In "sclerosing adenosis," or "fibrosing adenosis," the enlarged lobules are distorted by scar-like fibrous tissue.

As used herein, the term "cyst" refers to abnormal sacs filled with fluid or semi-solid material, and lined by breast epithelial cells, that develop from lobular structures. Cysts typically arise from excess fluid inside breast glands and may grow to proportions that stretch surrounding breast tissue, and thus cause pain. "Fibrocysts" are cystic lesions circumscribed by, or situated within, a conspicuous amount of fibrous connective tissue.

As used herein, the term "duct ectasia" refers to a dilation of mammary ducts by lipid and cellular debris. Rupture of the ducts induces infiltration by granulocytes and plasma cells.

As used herein, the term "fibroadenoma" refers to benign tumors that are derived from glandular epithelium and contain a conspicuous stroma of proliferating fibroblasts and connective tissue.

As used herein, the term "fibrosis" refers to a prominence of fibrous tissue in the breast.

The terms "somatostatin analog(s)", "SST analogs", "somatostatin" and any variants not specifically listed, may be used herein interchangeably, and as used throughout the present application and claims refer to proteinaceous material including single or multiple proteins or non-proteinaceous materials, and extends to those proteins having somatostatin or somatostatin-like activities, including the ability to bind to and/or otherwise modulate one or more somatostatin receptors SSTR1-SSTR5. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "somatostatin analog(s)", "SST analogs", "somatostatin" are intended to include within their scope proteins specifically recited herein as well as all substantially homologous analogs and allelic variations.

Somatostatins bind somatostatin receptor(s), with subtypes SSTR-1 to SSTR-5 identified, cloned, and functionally characterized (Patel Y C et al (1995) Life Sci 57:1249-1265;

Patel Y C et al (1996) Metabolism 45 (suppl 1):31-38; Reisine T and Bell G I (1995) Endocrin Rev 16:427-442; Buscail L et al (1995) PNAS USA 92:1580-1584; Bell G I and Reisine T (1993) Trends Neurosci 16:34-38). Octreotide and vapreotide have a low affinity for SSTR-1, a high affinity for SSTR-2, and moderate affinity for SSTR-3, SSTR-4 and SSTR-5.

The somatostatin analog SOM230 prevents mammary development in rats via two mechanisms (Ruan, W et al (2006) Mol Endocrinology 20(2):426-436). One of them is an inhibitory effect on growth hormone secretion from the pituitary which can cause reduction of serum IGF-I. The other is a direct inhibition of IGF-I action in the mammary gland as demonstrated by a reduction in IRS-1 phosphorylation in the mammary gland. It has been postulated that this effect of SOM230 is mediated by either somatostatin receptor subtype (SSTR) 3 or 5 and that this causes an increase in IGF binding protein 5 (IGFBP5) which in turn blocks the local action of IGF-I in the mammary gland (Ruan, W et al (2006) Mol Endocrinology 20(2):426-436). Somatostatin analog SOM 230 is the subject of a patent application of Novartis (U.S. Ser. No. 10/343,288, published as US2005/0014686; corresponding to PCT/EP01/08824, published as WO 02/01092A3; priority Aug. 1, 2000). This Application describes the compound, compositions thereof, and method of preventing or treating disorders with an etiology comprising or associated with excess GH-secretion and/or excess IGF-1, the entire contents of which is incorporated herein in its entirety Thus, in a particular aspect, methods are provided for prevention of breast cancer in a mammal diagnosed with cystic breast disease. In a particular aspect thereof, the mammal diagnosed with cystic breast disease is a BRCA1 patient. Such methods may comprise administration of one or more somatostatin analogs which has affinity for SSTR3 and/or SSTR5 somatostatin receptors. The use of one or more somatostatin analogs or other compound with enhanced affinity for SSTR3 and/or SSTR5 receptors, particularly versus SSTR1 and/or SSTR4 receptors in the treatment of non-proliferative cystic disease of the breast and in the prevention of breast cancer in individuals with non-proliferative cystic disease of the breast is provided. The exemplary compound SOM230 has affinity for SSTR3 and/or SSTR5 receptors.

Somatostatin analogs and/or other compounds which bind or otherwise associate with and activate/signal the SSTR3 and/or SSTR5 receptors are suitable for use in the invention. The action of a somatostatin analog and its ability or capability to bind to or otherwise associate with SSTR3 and/or SSTR5 somatostatin receptor(s) can be determined by the skilled artisan by recognized or herein disclosed methods. Somatostatin analogs include but are not limited to BIM23A779 (Neuroendocrinology 83:258-263, 2006), AN-238 (Clin Cancer Research 7:2854-2861, 2001) (2-pyrrolinodoxorubicin (AN-201) linked to octapeptide carrier RC-121) (Nagy A et al (1998) Proc Natl Acad Sci USA 95:1794-1799), RC-121 (D-Phe-Cys-Tyr-D-Trp-Lys-Val-Cys-THr-NH2) (Cai, R-Z et al (1986) Proc Natl Acad Sci USA 83:1896-1900), cyclic somatostatin analog peptide which selectively binds to the SRIF receptor SSTR3 (described in U.S. Pat. No. 6,579,967), Somatostatin Tumor Inhibiting Analog (Anaspec). Nikiforovich has used molecular modeling of constrained somatostatin analog peptides to probe SSTR specificity (Nikiforovich G V et al (2007) Chemical Biology and Drug Design 69(3):163-169). These studies serve as templates for design of conformationally-constrained non-peptide scaffolds that interact with specific SSTR subtypes.

One skilled in the art can readily determine or assess the suitability of other compounds for use in the invention, including by screening in a hyperplastic disorder and cystic disease model (such as described herein), or by determining its binding to and/or specificity for SSTR 3 and/or SSTR5 receptors, particularly in the breast.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
| --- | --- | --- |
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Mutations can be made in the sequence of a somatostatin and/or somatostatin analog or compound of use in the invention such as to provide adequate amino acid. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino acids with nonpolar R groups
Alanine, Valine, Leucine, Isoleucine, Proline, Phenylalanine, Tryptophan, Methionine
Amino acids with uncharged polar R groups
Glycine, Serine, Threonine, Cysteine, Tyrosine, Asparagine, Glutamine
Amino acids with charged polar R groups (negatively charged at Ph 6.0)
Aspartic acid, Glutamic acid
Basic amino acids (positively charged at pH 6.0)
Lysine, Arginine, Histidine (at pH 6.0)
Another grouping may be those amino acids with phenyl groups:
Phenylalanine, Tryptophan, Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

The compounds, somatostatin or somatostatin analogs of use in the invention may be prepared in pharmaceutical compositions, with a suitable carrier and at a strength effective for administration by various means to a patient experiencing an adverse medical condition associated with hyperplastic disorders and cystic disease of the breast and/or enhanced risk of breast cancer for the treatment thereof. A variety of administrative techniques may be utilized, among them parenteral techniques such as subcutaneous, intravenous and intraperitoneal injections, catheterizations and the like. Average quantities of the compounds, somatostatins, somatostatin analogs or their subunits may vary and in particular should be based upon the recommendations and prescription of a qualified physician or veterinarian.

Also, antibodies including both polyclonal and monoclonal antibodies, and drugs that modulate the production or activity of the somatostatins, and/or somatostatin receptors, particularly SSTR3 and/or SSTR5, may possess certain diagnostic applications and may for example, be utilized for the purpose of detecting and/or measuring conditions such as viral infection or the like. For example, the somatostatins, somatostatin analogs or their receptors may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the somatostatin analogs of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against somatostatins, and/or somatostatin receptor peptides can be screened for various properties; i.e., isotype, epitope, affinity, etc. Such monoclonals can be readily identified in activity assays. High affinity antibodies are also useful when immunoaffinity purification of native or recombinant somatostatins, somatostatin analogs or somatostatin receptors is possible or warranted.

Preferably, the anti-somatostatin or SSTR antibody used in the diagnostic methods of this invention is an affinity purified polyclonal antibody. More preferably, the antibody is a monoclonal antibody (mAb). In addition, it is preferable for the anti-somatostatin or SSTR antibody molecules used herein be in the form of Fab, Fab', F(ab')$_2$ or F(v) portions of whole antibody molecules.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal antibodies are also well-known in the art. See Niman et al., *Proc. Natl. Acad. Sci. USA*, 80:4949-4953 (1983). Typically, the somatostatin, somatostatin analogs or SSTR or a peptide analog is used either alone or conjugated to an immunogenic carrier, as the immunogen in the before described procedure for producing anti-somatostatin, somatostatin analogs or SSTR monoclonal antibodies. The hybridomas are screened for the ability to produce an antibody that immunoreacts with the somatostatin, somatostatin analogs or SSTR.

In contrast to expectations that mice comprising loxP sites flanking exon 11 of the BRCA1 gene (also referred to herein as LoxP mice) would develop normally, the present inventor found that at 4 months of age they had highly abnormal development including the formation of HANs, which are preneoplastic gland collections. Interestingly, when these animals were treated with SOM230, the inventor found that such treatment had a significant effect on inhibiting abnormal ductal dilatation and preventing formation of HANs. In light of the evidence presented herein, the inventor has identified an animal model system wherein SOM230 and other agents (alone or in combination) can be evaluated to determine if they prevent abnormal mammary gland development. The results presented herein also reveal that once pubertal mammary development is complete, and the gland quiescent, SOM230 no longer has an inhibitory effect like it does during active development (Ruan et al. Mol Endocrinol 2006, 20:426-436).

Accordingly, the present inventor has made the surprising discovery that the LoxP mice provide an animal model system that is well suited to screening agents to assess their ability to prevent abnormal mammary gland development. The LoxP mouse model system benefits from the features that the animals are easy to breed and display disease early in life. Accordingly, the LoxP mouse system provides a superior model system in that it recapitulates the temporal window in which premalignant conditions, such as hyperplastic disorders and cystic disease, or malignant disease can present in humans. See FIG. 14 for comparative timeline depicting lifespan and premalignant and malignant disease onset. To the best of the present inventor's knowledge, the LoxP animal system offers the earliest onset and most penetrant animal model system available to date for evaluating abnormal mammary gland development and screening agents for their ability to inhibit same. In certain embodiments, agents to be screened may be functionally and/or structurally related to SOM230 or any other inhibitory agent described herein. In other embodiments, agents may be screened without previous knowledge of their structure and/or function.

FIGS. 1 and 2, for example, portray the mammary gland phenotype in a 4 month old female mouse with the loxP sites flanking exon 11 of the BRCA1 gene as compared to a wild-type C57BL/6 control. As shown herein, control animals have relatively unadorned ducts and no TEBs after having gone through pubertal development, whereas the affected gland in LoxP females displays huge ductal dilation and pre-malignant HANs (hyperplastic alveolar nodules). Treatment of affected animals with SOM230 or control vehicle for 1 week revealed that the number of ducts was unchanged by SOM230, but the duct width was significantly reduced by SOM230 in the affected animals but not the wild type controls. See, for example, FIGS. 6-9. These results demonstrate that once pubertal ductal morphogenesis is complete and the gland is not under sufficient hormonal stimulation to further develop, inhibition of IGF-I action can no longer reverse that process. In contrast, in the case of the affected animals that are still undergoing new formation of HANs and dilatation of ducts, SOM230 can prevent or reverse such premalignant, abnormal events. Accordingly, the LoxP mouse model system described herein can be used for screening to identify agents that are capable of delaying and/or inhibiting the development of the premalignant conditions using the methodology and assays described herein for SOM230, PQ401, and SS14.

The present invention further contemplates therapeutic compositions useful in practicing the therapeutic methods of this invention. A subject therapeutic composition includes, in admixture, a pharmaceutically acceptable excipient (carrier) and one or more of a somatostatin, somatostatin analogs, polypeptide analog thereof or fragment thereof, as described herein as an active ingredient.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method may be used to create analogs with unnatural amino acids.

The presence of SSTR3 and/or SSTR5 in cells can be ascertained by the usual immunological procedures applicable to such determinations. A number of useful procedures are known. Three such procedures which are especially useful utilize either the somatostatin, somatostatin analog or SSTR labeled with a detectable label, antibody $Ab_1$ labeled with a detectable label, or antibody $Ab_2$ labeled with a detectable label. The procedures may be summarized by the following equations wherein the asterisk indicates that the particle is labeled, and "⁻" stands for the somatostatin, somatostatin analog or SSTR:

$$^-*+Ab_1=^-*Ab_1 \qquad \text{A.}$$

$$^-+Ab^*=^-Ab_1^* \qquad \text{B.}$$

$$^-+Ab_1+Ab_2^*=^-Ab_1Ab_2^* \qquad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the somatostatin, somatostatin analog or SSTR forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-somatostatin, somatostatin analog or SSTR antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

The present invention relates generally to the use and application of compounds or agents, including somatostatin analogs, with effect on, affinity for, or specificity to SSTR3 and/or SSTR5 somatostatin receptors, particularly in the breast, for the treatment of breast non-proliferative cystic disease and/or prevention or reduction of risk for breast cancer. The invention also relates to use of somatostatin analog SOM230 in treatment of breast non-proliferative cystic disease and/or prevention of breast cancer.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The somatostatin receptor(s) or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the somatostatin, somatostatin analog or SSTR may be radiolabeled and combined, for example, with antibodies or other inhibitors thereto, after which binding studies would be carried out. Solutions would then be prepared that contain various quantities of labeled and unlabeled uncombined somatostatin, somatostatin analog or SSTR, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn.

While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined somatostatin, somatostatin analog or SSTR activity or predetermined somatostatin, somatostatin analog or SSTR activity capability in suspected target cells. In accordance with the testing techniques discussed above, one class of such kits will contain at least the labeled somatostatin, somatostatin analog or SSTR or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined somatostatin, somatostatin analog or SSTR activity, comprising:

(a) a predetermined amount of at least one labeled immunochemically reactive component obtained by the direct or indirect attachment of the somatostatin, somatostatin analog or SSTR or a specific binding partner thereto, to a detectable label;
(b) other reagents; and
(c) directions for use of said kit.

More specifically, the diagnostic test kit may comprise:

(a) a known amount of the somatostatin, somatostatin analog or SSTR as described above (or a binding partner) generally bound to a solid phase to form an immunosorbent, or in the alternative, bound to a suitable tag, or plural such end products, etc. (or their binding partners) one of each;
(b) if necessary, other reagents; and
(c) directions for use of said test kit.

In a further variation, the test kit may be prepared and used for the purposes stated above, which operates according to a predetermined protocol (e.g. "competitive," "sandwich," "double antibody," etc.), and comprises:
  (a) a labeled component which has been obtained by coupling the somatostatin, somatostatin analog or SSTR to a detectable label;
  (b) one or more additional immunochemical reagents of which at least one reagent is a ligand or an immobilized ligand, which ligand is selected from the group consisting of:
    (i) a ligand capable of binding with the labeled component (a);
    (ii) a ligand capable of binding with a binding partner of the labeled component (a);
    (iii) a ligand capable of binding with at least one of the component(s) to be determined; and
    (iv) a ligand capable of binding with at least one of the binding partners of at least one of the component(s) to be determined; and
  (c) directions for the performance of a protocol for the detection and/or determination of one or more components of an immunochemical reaction between the somatostatin, somatostatin analog or SSTR and a specific binding partner thereto.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

The present inventor has made the surprising discovery that mice comprising loxP sites flanking exon 11 of the BRCA1 gene (formally known as $Brca1^{loxP/loxP}$, but also referred to herein as LoxP mice) display profoundly abnormal mammary gland development at an early age. LoxP mice were acquired from the National Institutes of Health Mouse Repository. The strain is Stock $Brca1^{tm2Cxd}$ and the Strain code is 01XC8. Mice were maintained in accordance with the standards established by the Association for Assessment and Accreditation of Laboratory Animal Care (AAALAC) (New York University). Animals so obtained were bred and assessed as described herein and LoxP mice exhibit abnormal mammary gland development typified by the appearance of dilated ducts and areas of dysplasia and hyperplasia in the mammary glands by the age of four months.

By way of background, exon 11 of BRCA1 accounts for 60% of the function of the entire gene (Xu et al. Nature Genetics 1999, 22:37-43). BRCA1 is a tumor suppressor gene that inhibits the actions of IGF-I (Maor et al. Cancer Lett 2007, 257:236-243; Hudelist et al. Endocr Relat Cancer 2007, 14:1053-1062), estradiol (Chand. 2009; Fan et al. Science 1999, 284:1354-1356), and progesterone (Ma et al. Mol Endocrinol 2006, 20:14-34.). When the gene is altered the actions of these three hormones are greatly enhanced, and the animals behave as if they are overexpressing all of them. Previous studies have shown that overexpression of IGF-I or GH can cause development of mammary carcinoma in animal models (Kleinberg et al. Endocr Rev 2009, 30:51-74).

FIG. 1 depicts the mammary gland phenotype in 4 month old $Brca1^{LoxP}/Brca1^{LoxP}$ mice. Representative whole mounts of mammary glands from a $Brca1^{LoxP}/Brca1^{LoxP}$ female and a C57Bl/6 control are shown. The mean width of mammary ducts in five $Brca1^{LoxP}/Brca1^{LoxP}$ mice and five C57Bl/6 controls is presented in the graph presented therein. Mammary gland morphology in $Brca1^{LoxP}/Brca1^{LoxP}$ mice is grossly abnormal, as reflected in significantly enlarged ductal width in these mice. The presence of hyperplastic alveolar nodules (HAN) in $Brca1^{LoxP}/Brca1^{LoxP}$ mice is also apparent. FIG. 2, for example, shows a i representative whole mount (left) and hematoxylin-eosin stained sections of the HAN-like lesions that can be observed in mammary gland from $Brca1^{LoxP}/Brca1^{LoxP}$ females starting from the age of 4 months.

To evaluate the status of BRCA mRNA transcripts in $Brca1^{LoxP}/Brca1^{LoxP}$ mice, RT-PCR for $\Delta 11$ Brca1 was performed by amplifying Brca1 cDNA with two primers spanning exon 10 and exon 14 of the gene. The experimental reasoning was that if exon 11 is present, as in the case of FL Brca1 mRNA, the gene fragment between the two primers will be too big to be amplified and no PCR product is found. On the contrary, if exon 11 is not present, as for $\Delta 11$ Brca1, the two primers will amplify a DNA fragment of 311 base pairs which can be visualized on agarose gel. RT-PCR for FL Brca1 was performed by amplifying Brca1 cDNA with two primers spanning exon 11 and exon 14 of the gene. When exon 11 is present, as in the case of FL Brca1 mRNA, these two primers amplify a 500 base pair DNA fragment that can be visualized on agarose gel.

Figure 3:
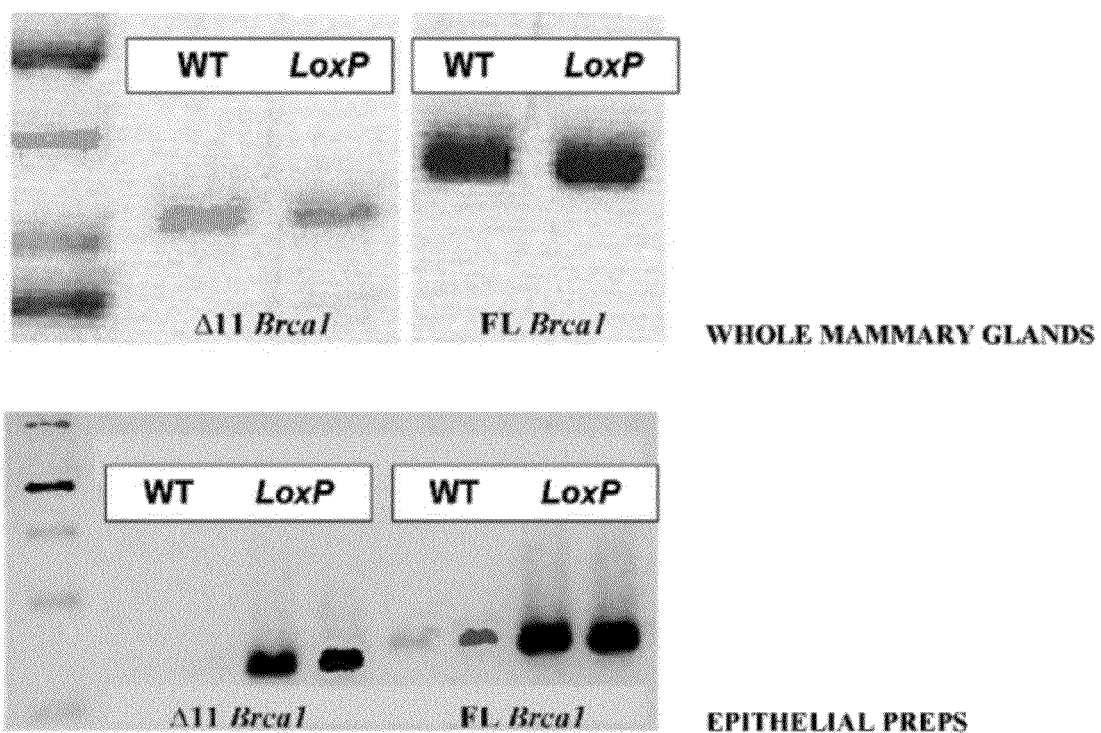
FIG. 3 depicts RT-PCR for Δ11 Brca1, which is obtained by alternative splicing of exon 11 of the Brca1 gene, and full-length (FL) Brca1, transcribed from the complete DNA sequence of the Brca1 gene. The upper Figure shows that both Δ11 and FL Brca1 mRNA transcripts are present in whole mammary gland lysates of both wild-type (WT) and LoxP mice. The lower Figure shows the results of RT-PCR on RNA extracts from epithelial cells isolated from mammary glands (epithelial preps) of WT and LoxP mice.
Figure 4:
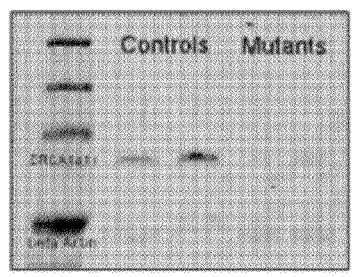
FIG. 4 shows BRCA1 proteins in Brca$^{LoxP}$/Brca1$^{LoxP}$ and C57Bl/6 mice. Western blot for BRCA1 performed with an antibody against the C-terminal of the protein, which is the same in both the full-length BRCA1 protein (BRCA1-FL) and the one translated from the mRNA obtained by alternative splicing of exon 11 (BRCA1$^{Δ11}$). BRCA1$^{Δ11}$ (80 KDa) is dramatically reduced in the Brca$^{LoxP}$/Brca1$^{LoxP}$ mutant mice, as opposed to controls.

The upper panel in FIG. 3 shows that both $\Delta 11$ and FL Brca1 mRNA transcripts are present in whole mammary gland lysates of both wild-type (WT) and LoxP mice. The lower panel of FIG. 3 shows the results of RT-PCR on RNA extracts from epithelial cells isolated from mammary glands (epithelial preps) of WT and LoxP mice. Since the expression of Brca1 is a function of cell proliferation, the apparent absence of $\Delta 11$ Brca1 mRNA in quiescent WT epithelial cells is believed to be due to a very low transcription rate, leading to production of such a small amount of mRNA that it cannot be detected by standard RT-PCR.

To summarize, a significant difference in levels of Brca1 $\Delta 11$ mRNA, as assayed by either qualitative or quantitative RT-PCR, was not observed in the LoxP animals when compared to controls. See FIG. 3.

FIG. 4 shows BRCA1 proteins expressed in $Brca1^{LoxP}/Brca1^{LoxP}$ and C57Bl/6 mice. Western blotting to detect BRCA1 proteins was performed using an antibody specific for the C-terminal of the protein, which is present in both full-length BRCA1 protein (BRCA1-FL) and the one translated from the mRNA obtained by alternative splicing of exon 11 (BRCA1$^{\Delta 11}$). BRCA1-FL has an expected size of 220 KDa, while the BRCA1$^{\Delta 11}$ has an expected size of 80 KDa. As shown therein, the expression of the $\Delta 11$ protein was decreased in comparison to wild type animals. In contrast BRCA1-FL is expressed similarly in controls and LoxP animals. These results suggest that the phenotypic changes observed in the LoxP animal model system are at least in part due to impaired expression of Brca1 $\Delta 11$.

Figure 5:
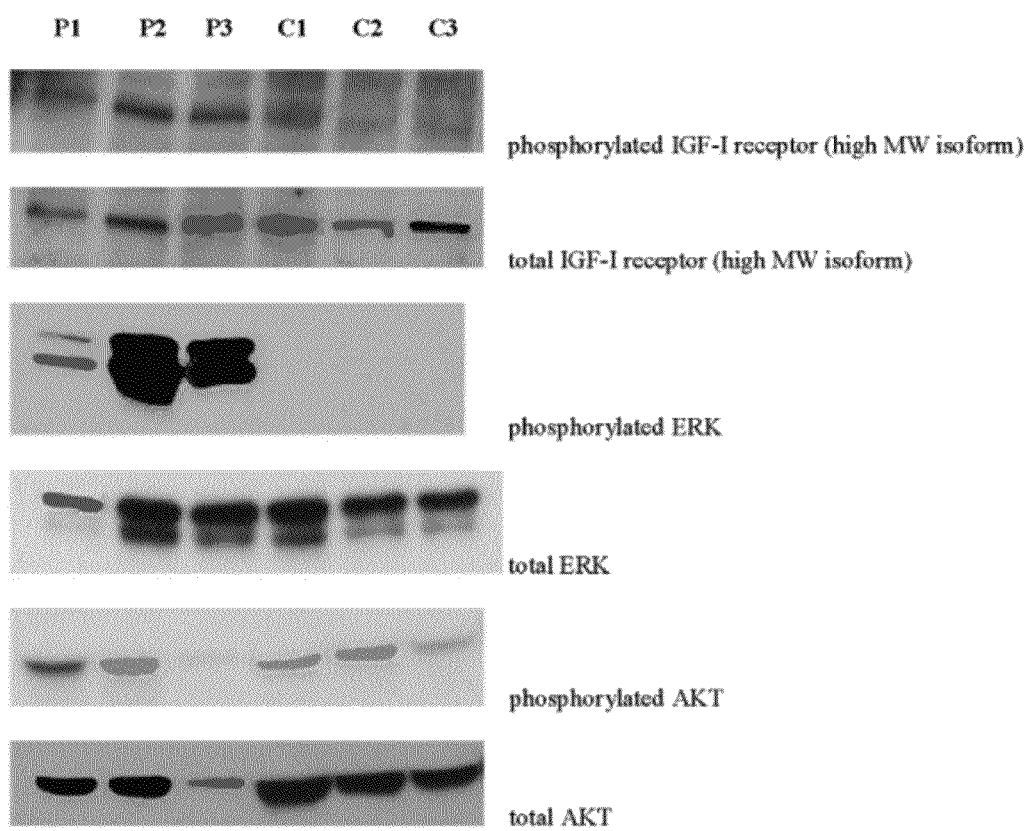
FIG. 5 depicts phosphorylation of IGF-I receptor, ERK, and AKT in 4 month old Brca1$^{LoxP}$/Brca1$^{LoxP}$ and C57Bl/6 mice. Representative Western blots showing that the phosphorylation of IGF-I receptor and its downstream mediators ERK and AKT is increased in Brca1$^{LoxP}$/Brca1$^{LoxP}$ females (samples P19, P21, P46) as compared with age-matched C57Bl/6 controls (samples C3, C4, and C5). MW: molecular weight.

FIG. 5 depicts the phosphorylation levels of IGF-I receptor, ERK, and AKT in 4 month old $Brca1^{LoxP}/Brca1^{LoxP}$ and C57Bl/6 mice. As shown therein, the phosphorylation of the IGF-I receptor and its downstream mediators ERK and AKT is increased in $Brca1^{LoxP}/Brca1^{LoxP}$ females (samples P19, P21, P46), as compared with age-matched C57Bl/6 controls (samples C3, C4, and C5). MW: molecular weight. These results demonstrate that the IGF-I receptor signaling pathway is activated in the Brca1$^{LoxP}$/Brca1$^{LoxP}$ mice, which is reminiscent of IGF-I receptor activation observed in mice homozygous for targeted deletion of full length BRCA1 (Skukla et al. 2006, Cancer Res 66:7151-7157).

FIG. 6 depicts Western blots showing the effects of IGF-I inhibition on the phosphorylation of IGF-I receptor, ERK, and AKT in 4 month old Brca1$^{LoxP}$/Brca1$^{LoxP}$. The increased phosphorylation of IGF-I receptor and its downstream mediators ERK and AKT in Brca1$^{LoxP}$/Brca1$^{LoxP}$ females is reduced by treatment with 100 mg/kg PQ401 thrice a week and 10 µg/kg/h pasireotide. The two WT samples are from age-matched, untreated C57Bl/6 control mice. PQ401 was administered by intraperitoneal injections, pasireotide by Alzet pump Model 2001. For both drugs, the course of treatment was 7 days. These results show that the activated state of the IGF-I receptor signaling pathway observed in the Brca1$^{LoxP}$/Brca1$^{LoxP}$ mice can be reduced and potentially abrogated by administration of either PQ401 or pasireotide.

Figure 7:
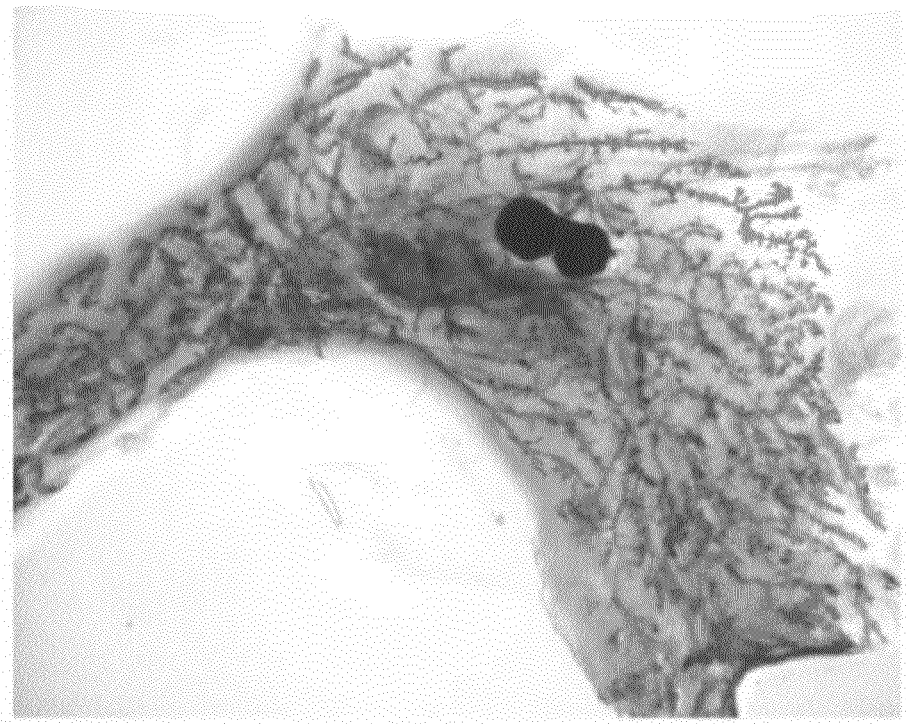
FIG. 7 shows effects of pasireotide on the mammary gland phenotype of Brca1$^{LoxP}$/Brca1$^{LoxP}$ mice. Representative whole mounts of mammary glands from 4 month old Brca1$^{LoxP}$/Brca1$^{LoxP}$ females treated with water (upper photomicrographs) or 10 µg/kg/h pasireotide (lower photomicrographs) for 7 days. Both water and pasireotide were administered by Alzet pump Model 2001.
Figure 7:

FIG. 7 shows the effects of pasireotide on the mammary gland phenotype of Brca1$^{LoxP}$/Brca1$^{LoxP}$ mice. Representative whole mounts of mammary glands from 4 month old Brca1$^{LoxP}$/Brca1$^{LoxP}$ females treated with water (upper photomicrographs) or 10 µg/kg/h pasireotide (lower photomicrographs) for 7 days are shown. Both water and pasireotide were administered by Alzet pump Model 2001. These results demonstrate that treatment with pasireotide dramatically reduces the mammary gland phenotype of Brca1$^{LoxP}$/Brca1$^{LoxP}$ mice. These findings were confirmed on a histological level as shown in FIG. 8 which depicts representative hematoxylin-eosin sections of mammary glands from 4 month old Brca1$^{LoxP}$/Brca1$^{LoxP}$ females treated with water (left) or pasireotide (center and right) for 7 days. Both water and pasireotide (10 µg/kg/h) were administered by Alzet pump Model 2001. FIG. 9 shows that pasireotide also reduces duct width of mammary glands of Brca1$^{LoxP}$/Brca1$^{LoxP}$ mice. More particularly, FIG. 9 shows that 10 µg/kg/h pasireotide for 7 days is effective in decreasing the width of mammary gland ducts in 4 month old Brca1$^{LoxP}$/Brca1$^{LoxP}$ females, as compared with vehicle (water). Both water and pasireotide were administered by Alzet pump Model 2001. These results definitively demonstrate that treatment with pasireotide dramatically reduces the mammary gland phenotype of Brca1$^{LoxP}$/Brca1$^{LoxP}$ mice as evaluated on a gross and histological level, including a reduction in ductal width.

Treatment with PQ401, a potent inhibitor of IGF-I receptor signaling and breast cancer cell growth in culture and in vivo, also dramatically reduces the mammary gland phenotype of Brca1$^{LoxP}$/Brca1$^{LoxP}$ mice. See FIG. 10. Representative whole mounts from mammary glands of 4 month old Brca1LoxP/Brca1LoxP females treated with PQ401 (upper microphotograph) or vehicle (8% ethanol/Tween 80 in PBS, lower microphotograph) for 7 days are shown. Both PQ401 and vehicle were administered by intraperitoneal injections.

FIG. 11 shows the percentage of Ki67-positive epithelial cells in the mammary glands of 4 month old Brca1$^{LoxP}$/Brca1$^{LoxP}$ mice after 7 days of treatment with pasireotide (LoxP, pasireotide), PQ401 (LoxP, PQ401), or vehicle (LoxP, water and LoxP, ethanol/Tween). The frequency of Ki67-positive mammary epithelial cells in C57Bl/6 controls treated with water (WT, water) is also presented. *, p<0.05 as compared with WT, water; **, p<0.01 as compared with WT, water; a, p<0.05 as compared with LoxP, water; b, p<0.01 as compared with LoxP, water. These results show that treatment with either pasireotide or PQ401 reduces the number of Ki67 positive epithelial cells in the mammary glands of 4 month old Brca1$^{LoxP}$/Brca1$^{LoxP}$ mice. This finding is significant because Ki67 is a cancer antigen that is found in growing, dividing cells, but is absent in the resting phase of cell growth. Accordingly, Ki67 is viewed as a good tumor cell marker. The present findings suggest, therefore, that administration of either pasireotide or PQ401 is an effective approach for reducing the mammary gland phenotype of Brca1$^{LoxP}$/Brca1$^{LoxP}$ mice and, by extension, those observed in humans at premalignant stages that may potentially lead to malignant breast cancer.

Figure 12:
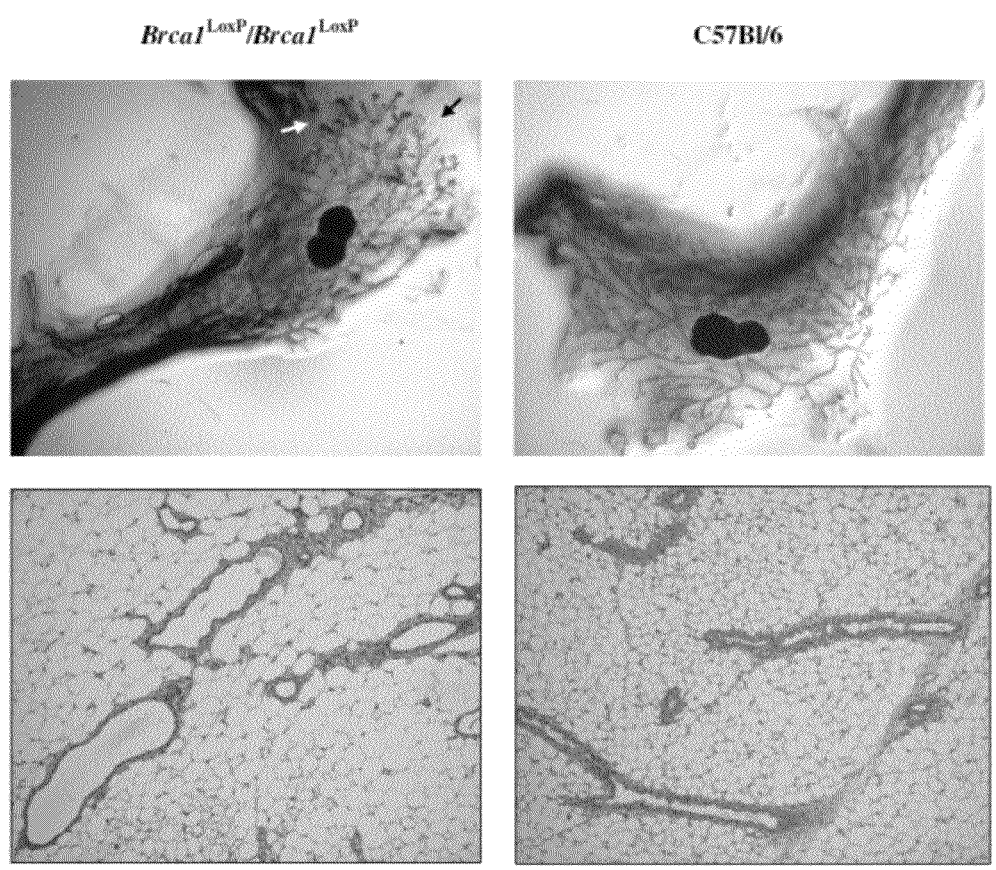
FIG. 12 depicts the mammary gland phenotype in Brca1$^{LoxP}$/Brca1$^{LoxP}$ (left) and C57Bl/6 control (right) mice at two months of age. Note the presence of terminal end buds (arrow), a sign of ongoing mammary development, in the whole mount from the Brca1$^{LoxP}$/Brca1$^{LoxP}$ animal, but not in the wild-type control (upper left and upper right, respectively). The lower photomicrographs are hematoxylin-eosin stained histological sections, showing that duct dilatation is already present at two months of age in Brca1$^{LoxP}$/Brca1$^{LoxP}$ animals as compared with controls.

To further investigate the onset of the abnormal breast and mammary phenotype observed in Brca1$^{LoxP}$/Brca1$^{LoxP}$ mice, two month old Brca1$^{LoxP}$/Brca1$^{LoxP}$ and control mice were examined. FIG. 12 depicts the mammary gland phenotype in Brca1$^{LoxP}$/Brca1$^{LoxP}$ and C57Bl/6 control mice at two months of age. The presence of terminal end buds (arrow), a sign of ongoing mammary development, is noteworthy in the whole mount from the Brca1$^{LoxP}$/Brca1$^{LoxP}$ animal. At two months of age, however, no ductal or lobular hyperplasia is observed in Brca1$^{LoxP}$/Brca1$^{LoxP}$ mice. In contrast, full mammary development has already taken place in two month old wild-type control animals and thus, terminal end buds are not observed in these animals. Another notable phenotypic distinction observed in two month old Brca1$^{LoxP}$/Brca1$^{LoxP}$ mice is the presence of enlarged ducts, which are not apparent in age matched C57Bl/6 control mice. The lower photomicrographs, which show hematoxylin-eosin stained histological sections, depict this distinctive phenotype by clearly showing that ductal dilation is already present in two month old Brca1$^{LoxP}$/Brca1$^{LoxP}$ animals as compared with controls.

For comparative purposes to human lifespan, two month old mice are in late puberty and 4 month old mice are adults. See FIG. 14. Accordingly, these findings are interesting in several respects. The early onset of the phenotype of non-proliferative cystic lesions, as evidenced by ductal dilation, in Brca1$^{LoxP}$/Brca1$^{LoxP}$ mice facilitates examination of phenotypic risk factors that appear earlier in life, in advance of benign hyperplastic disease onset. Moreover, the present inventors believe that the appearance of non-proliferative cystic lesions in Brca1$^{LoxP}$/Brca1$^{LoxP}$ mice recapitulates aspects of early disease onset believed to occur in BRCA1 associated disease in humans. No one has performed a study of the age at which such lesions occur in BRCA1 mutated patients, but almost 40% of BRCA1 patients have such lesions by the time they have elected to have prophylactic mastectomies, and breast cancer in BRCA1 patients can appear in the early 20s.

Examined in combination with the results presented in, for example, FIG. 1, several conclusions can be drawn. Although the phenotype of two month old Brca1$^{LoxP}$/Brca1$^{LoxP}$ mice is profoundly abnormal, it is less cystic than that observed in four month old Brca1$^{LoxP}$/Brca1$^{LoxP}$ mice and does not have areas of atypical hyperplasia characteristic of the four month old animals. Based on these results, the present inventor concludes that there is a temporal cascade of hyperactive mammary development, including ductal dilation (cystic disease), that develops by late puberty in Brca1$^{LoxP}$/Brca1$^{LoxP}$ mice (at two months) and further develops into a phenotype of greater duct dilation and the beginning of atypical hyperplasia, as observed in adult Brca1$^{LoxP}$/Brca1$^{LoxP}$ mice (at four months). As Brca1$^{LoxP}$/Brca1$^{LoxP}$ mice age past four months, the ducts fail to enlarge further and may indeed decrease in size, while atypical hyperplasia reaches a maximal level. These findings support a progression from non-proliferative cystic disease of the breast to cystic disease in combination with atypical hyperplasia, which in turn, leads to malignant breast cancer.

Figure 13:
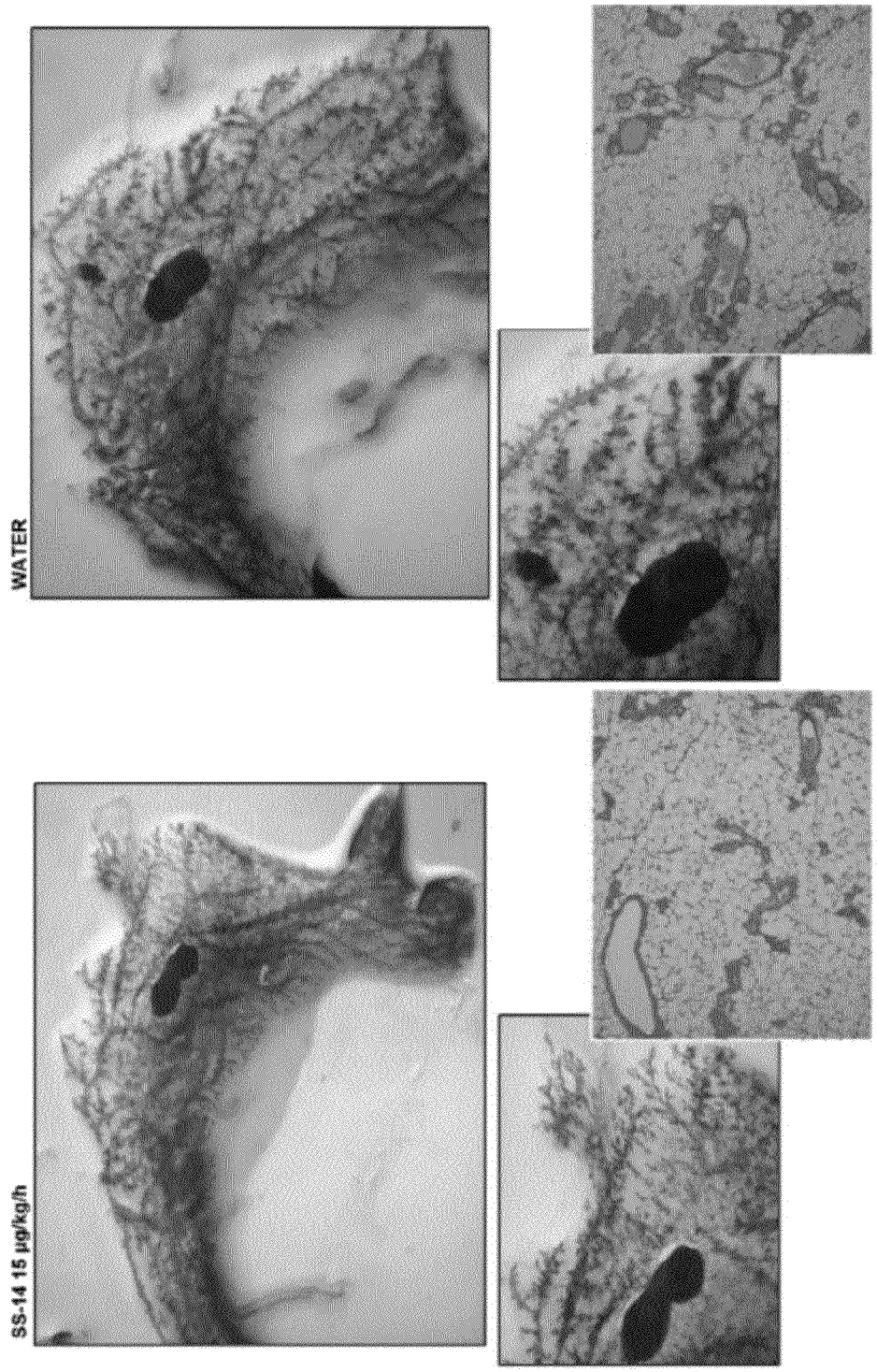
FIG. 13 depicts effect of somatostatin-14 on the mammary gland phenotype of Brca1$^{LoxP}$/Brca1$^{LoxP}$ mice. Representative whole mounts and hematoxylin-eosin stained sections of mammary glands from 9 month old Brca1Loxp/Brca1LoxP females treated with somatostatin-14 (SS-14, left) or vehicle (water, right) for 7 days. Both SS-14 and water were administered by Alzet pump Model 2001.

FIG. 13 depicts effects of somatostatin-14 on the mammary gland phenotype of Brca1$^{LoxP}$/Brca1$^{LoxP}$ mice. Representative whole mounts and hematoxylin-eosin stained sections of mammary glands from 9 month old Brca1$^{LoxP}$/

Brca1$^{LoxP}$ females treated with somatostatin-14 (SS-14, left) or vehicle (water, right) for 7 days are shown. Both SS-14 and water were administered by Alzet pump Model 2001. These results show that treatment with SS-14 reduces the mammary gland phenotype, even in older Brca1$^{LoxP}$/Brca1$^{LoxP}$ mice. These results indicate that administration of SS-14 is an effective approach for reducing the mammary gland phenotype of Brca1$^{LoxP}$/Brca1$^{LoxP}$ mice and similar phenotypic changes observed in humans at premalignant stages that may potentially be precursors of malignant breast cancer.

FIG. 14 shows a comparative time line for mouse and human lifespans and typical age of disease manifestation.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for treating non-proliferative cystic disease of the breast in a mammal comprising selecting a mammal having enlarged mammary ducts without detected atypical hyperplasia of the breast and administering to said mammal a therapeutically effective amount of at least one inhibitor of insulin-like growth factor I (IGF-I) or insulin-like growth factor I receptor signaling, wherein the administering reduces mammary duct width in the mammal, thereby treating the mammal and wherein the mammal cannot tolerate side effects of anti-estrogenic compounds.

2. A method for providing symptomatic relief to a mammal afflicted with non-proliferative cystic disease of the breast, the method comprising selecting a mammal having enlarged mammary ducts without detected atypical hyperplasia of the breast and administering to the mammal a therapeutically effective amount of at least one inhibitor of insulin-like growth factor I (IGF-I) or insulin-like growth factor I receptor signaling, wherein the administering confers a reduction in pain, discomfort, and/or lumpiness associated with the enlarged mammary ducts, thereby providing symptomatic relief to the mammal and wherein the mammal cannot tolerate side effects of anti-estrogenic compounds.

3. The method of claim 1 or 2, wherein the at least one inhibitor is a somatostatin analog, or an antibody or small molecule inhibitor of IGF-I action on the IGF-I receptor.

4. The method of claim 1, wherein the mammal is a BRCA1 mutation carrier.

5. The method of claim 3, wherein the somatostatin analog is selected from SOM230, somatostatin 14, SMS 201-995, BIM 23014, BIM23A779, AN-238, RC-121, cyclic somatostatin analog peptide, and somatostatin tumor inhibiting analog.

6. The method of claim 3, wherein the somatostatin analog has enhanced affinity for SSTR3 receptors and SSTR5 receptors relative to that for SSTR1 and/or SSTR4 receptors.

7. The method of claim 1, wherein the mammal is a human.

8. The method of claim 2, wherein the mammal is a human.

* * * * *